(12) United States Patent
Mikami et al.

(10) Patent No.: US 9,969,996 B2
(45) Date of Patent: May 15, 2018

(54) METHOD FOR MAKING MUTATED PULLULANASE ENZYME, MUTATED PULLULANASE ENZYME, AND MICROORGANISM EXPRESSING THE SAME

(71) Applicant: Amano Enzyme Inc., Nagoya-shi (JP)

(72) Inventors: Bunzo Mikami, Uji (JP); Hiroyuki Iwamoto, Fukuyama (JP); Shotaro Yamaguchi, Kakamigahara (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days. days.

(21) Appl. No.: 14/983,447

(22) Filed: Dec. 29, 2015

(65) Prior Publication Data

US 2016/0194620 A1 Jul. 7, 2016

Related U.S. Application Data

(63) Continuation-in-part of application No. 12/309,929, filed as application No. PCT/JP2007/062996 on Jun. 28, 2007, now abandoned.

(30) Foreign Application Priority Data

Aug. 4, 2006 (JP) .................. 2006-213490

(51) Int. Cl.
*C12N 9/44* (2006.01)

(52) U.S. Cl.
CPC .... *C12N 9/2457* (2013.01); *C12Y 302/01041* (2013.01)

(58) Field of Classification Search
None
See application file for complete search history.

(56) References Cited

U.S. PATENT DOCUMENTS

| | | | |
|---|---|---|---|
| 6,265,197 B1 | 7/2001 | Bisgard-Frantzen et al. | |
| 2003/0022348 A1 | 1/2003 | Miller et al. | |

FOREIGN PATENT DOCUMENTS

| | | |
|---|---|---|
| EP | 0 605 040 A1 | 7/1994 |
| JP | 05-292962 | 11/1993 |
| JP | 07-289186 | 11/1995 |
| JP | 2002-505108 | 2/2002 |
| JP | 2002-519054 | 7/2002 |
| JP | 2006-174841 A | 7/2006 |
| WO | WO-9945124 A2 | 9/1999 |
| WO | WO-0001796 A2 | 1/2000 |
| WO | WO-01/51620 A2 | 7/2001 |

OTHER PUBLICATIONS

USPTO in house NCBI BLAST alignment of SEQ ID No. 2 vs SEQ ID No. 13. Performed Apr. 28, 2017.*
Metzler et al, Enzymes: The Protein Catalysts of Cells. In: Biochemistry, The Chemical Reactions of Living Cells Second Edition 2001. Harcort/ Academic Press, Inc. New York, NY p. 455-533 (Chapter 9).*
Examination Report, dated Apr. 13, 2016, for EP Application No. 13 179 288.9.
Database EMBL [Online] Sep. 2, 1993 (Sep. 2, 1993), "Klebsiella pneumoniae DNA sequence.", retrieved from EBI accession No. EMBL:L19312 Database accession No. L19312.
Database Geneseq [Online] Mar. 25, 2003 (Mar. 25, 2003), "Polypeptide with isoamylase activity from Pseudomonas amyloderamosa.", retrieved from EBI accession No. GSP:AAP90615 Database accession No. AAP90615.
BLAST alignment GenBank Acc. No. AA000283 (SEQ ID No. 2) vs GenBank Acc. No. BAA11332.1 from Hatada et al, J Biol Chem. Sep. 27, 1996;271(39):24075-83.
Database Geneseq [Online] Jul. 29, 2004 "Klebsiella Pneumoniae Polypeptide Sequid 12330" Accession No. AB065813.
Database Geneseq [Online] dated Mar. 11, 1998 "Trimmed Enzyme Protein" Accession No. AAW37372.
Database Geneseq [Online] dated Feb. 9, 2006 "Bacterial Pullulanase Protein Sequence" Accession No. AEE27547.
Database UniProt [Online] Jul. 1, 1989 "RecName: Full=Isoamylase; EC-3.2.1.68; Flags: Precursor". Accession No. P10342.
Database UniProt [Online] Mar. 1, 2005 (Mar. 1, 2005), "SubName: Full=Thermostablepullulanase; EC=3.2.1.41", retrieved from EBI accession No. UNIPROT:Unreviewed Database accession No. Unreviewed.
Database UniProt [Online] Oct. 25, 2004 (Oct. 25, 2004), "SubName: Full=Pullulanase; EC=3.2.1.41", retrieved from EBI accession No. UNIPROT:Q63AL5 Database accession No. Q63AL5.
Database UniProt [Online] XP-002540760, Jan. 1, 1998, 2 pages. E.C.# 3.2.1.10, 3.2.1.41, and 3.2.1.70; alpha -1,6-glucosidase from BRENDA.
EP Patent Office correspondence pursuant to Article 94(3) EPC dated Aug. 18, 2014 issued in corresponding European Divisional Application No. 13179288.9.
Extended European Search Report from EP Application No. 13179288.9-1402, dated Jan. 2, 2014.
Galye et al, Identification of regions in interleukin-1 alpha important for activity. J Biol Chem. Oct. 15, 1993;268(29):22105-11.

(Continued)

*Primary Examiner* — Sheridan Swope
(74) *Attorney, Agent, or Firm* — Locke Lord LLP; James E. Armstrong, IV; Nicholas R. Herrel

(57) ABSTRACT

A method for making a mutated pullulanase enzyme that hydrolyzes an α-1,6-glycosidic linkage is provided. The method includes obtaining the amino acid sequence of a pullulanase enzyme having an amino acid sequence that is at least 95% identical to the amino acid sequence set forth in SEQ ID NO: 13; identifying an amino acid to be mutated in the pullulanase enzyme of step (1), wherein the amino acid to be mutated corresponds to the amino acid at position Phe476 of SEQ ID NO: 2; constructing a mutated amino acid sequence by substituting the amino acid to be mutated with another amino acid or deleting the amino acid to be mutated, thereby making a mutated pullulanase enzyme having the mutated amino acid sequence that has increased affinity for pullulan and that hydrolyzes an α-1,6-glycosidic linkage.

5 Claims, 9 Drawing Sheets

(56) References Cited

OTHER PUBLICATIONS

Hatada et al, Amino acid sequence and molecular structure of an alkaline amylopullulanase from Bacillus that hydrolyzes alpha-1,4 and alpha-1,6 linkages in polysaccharides at different active sites. J Biol Chem. Sep. 27, 1996;271(39):24075-83.
Internation Search Report dated Sep. 4, 2007, issued on PCT/JP2007/062996.
Mikami et al, Crystal Structure of Pullulanase: Evidence for Parallel Binding of Oligosaccharides in the Active Site. J Mol Biol. Jun. 9, 2006;359(3):690-707. Epub Apr. 18, 2006.
Park and Johnson, "A submicrodetermination of glucose." J. Biol Chem. Nov. 1949;181(1):149-51.
Supplemental European Search Report dated Aug. 27, 2009, issued on the corresponding European application No. 07 76 7790.4.
Whisstock et al, Prediction of protein function from protein sequence and structure. Q Rev Biophys. Aug. 2003;36(3):307-40. Review.

* cited by examiner

BSP/KPP

BSP/PIA

| | | |
|---|---|---|
| BSP | 1 | MVSIRRSFEAYVDDMNIITVLIPAEQKEIMTPPFRLETEITD-FPLAVREEYSLEAKYKY 59 |
| BLP | 1 | MPGISRPFEAYLDEMRTITVLVPKSRASSCSPPFLLEDDQGERIELSVKAQVELEEQFKY 60 |

| | | |
|---|---|---|
| BSP | 60 | VCVSDHPVTFGKIHCVRASSGHKTDLQIGAVIRTAAFDDEFYYDGELGAVYTADHTVFKV 119 |
| BLP | 61 | VLESSCTVPFGRVHKVCCEESVWTDLQIGSVTRSAAFDKAFFYDGRLGAFYSKGSTLFKV 120 |

| | | |
|---|---|---|
| BSP | 120 | WAPAATSAAVKLSHPNK--SGRTFQMTRLEKGVYAVTVTGDLHGYEYLFCICNNSEWMETV 178 |
| BLP | 121 | WAPTASAAAIKLEDPDSLQTNTFQMMRRKKGVFEVTVEGDLNGWSYLYELYVNGKPLLTV 180 |

| | | |
|---|---|---|
| BSP | 179 | DQYAKAVTVNGEKGVVLRPDQMKWTAPLKPFSH--PVDAVIYETHLRDFSIHENSGMINKG 237 |
| BLP | 181 | DPYAKAVTANGEKGVVLDPEEVKVEKHRAPRLHSPCDAVIYEVHIRDFSIHEDSGMRHKG 240 |

| | | |
|---|---|---|
| BSP | 238 | KYLALTETDTQTANGSSSGLAYVKELGVTHVELLPVNDFAGVDEEKPLDAYNWGYNPLHF 297 |
| BLP | 241 | KYVAFTEDGTETSGGFSTGIAYLKELGVTHIEVLPFHDFAGVDELSPDQSYNWGYNPLHF 300 |

Pul/Iso specific region

| | | |
|---|---|---|
| BSP | 298 | FAPEGSYASNPHDPQTRKTELKQMINTLHQHGLRVILDVVFNHVYKRENSPFEKTVPGYF 357 |
| BLP | 301 | NAPEGSYSLDPQNPKCRITELKTMIQSLHKHGFSVIMDAVYNHVYKRETSPFEKTVPGYF 360 | region I

| | | |
|---|---|---|
| BSP | 358 | FRHDECGMPSNGTGVGNDIASERRMARKFIADCVVYWLEEYNVDGFRFDLLGILDIDTVL 417 |
| BLP | 361 | FRHNEYGFPSDGTGVGNDIASERLMVRKYILDSVRYWLEEYDVDGIRFDLMGILDIETVR 420 | region II

| | | |
|---|---|---|
| BSP | 418 | YMKEKATKAKPGILLFGEGWDLATPLPHEQKAALANAPRMPGIGFFNDMFRDAVKGNTFH 477 |
| BLP | 421 | QISTLAENVKPGVLLFGEGWDLNTPLDSGQKATLQNAGKVPAVGFFNDRFRNAVKGSTFE 480 | region III

| | | |
|---|---|---|
| BSP | 478 | LKATGFALGNGESAQAVMHGIAGSSGWKALAPIVPEPSQSINYVESHDNHTFWDKMSFAL 537 |
| BLP | 481 | LSDRGYALGDTGKKAALQHGIAGSPGFL----------QPAQSINYVECHDNHTFWDKMALCF 533 | region IV

| | | |
|---|---|---|
| BSP | 538 | PQENDSRKRSRQRLAVAIILLAQGVPFIHSGQEFFRTKQGVENSYQSSDSINQLDWDRRE 597 |
| BLP | 534 | EEDADT-KRLRQRLAVSIVLLSQGVPFLHAGQEFCRTKNGDSNSYRSGDDINKLDWEKRA 592 |

| | | |
|---|---|---|
| BSP | 598 | TFKEDVHYIRRLISLRKAHPAFRLRSAADIQRHLECLTLKEHLIAYRLYDLDEVDEWKDI 657 |
| BLP | 593 | ELCEDVEYVRQLIRLRRSHPAFRLQKEEEVKEHLSFMDGTGEVTAYKLKNIAAIDPWNEI 652 |

| | | |
|---|---|---|
| BSP | 658 | IVIHHASPDSVEWRLPNDIPYRLLCDPSGFQEDPTEIKKTVAVNGIGTVILY 709 (SEQ ID NO:2) |
| BLP | 653 | IVVHCPFAKKETLKLPDQKQYLLHCDPFTFFNGKVQAEKRLRLNGIGTYVLY 704 (SEQ ID NO:17) |

```
                              SEQUENCE LISTING

<160> NUMBER OF SEQ ID NOS: 17

<210> SEQ ID NO 1
<211> LENGTH: 2233
<212> TYPE: DNA
<213> ORGANISM: Bacillus subtilis

<400> SEQUENCE: 1
atggtcagca tccgccgcag cttcgaagcg tatgtcgatg acatgaatat cattactgtt      60
ctgattcctg ctgaacaaaa ggaaatcatg acaccgccgt ttcggcttga gacagaaata     120
acagattttc ctctggctgt cagggaggaa tactcccttg aagcaaaata caagtacgtc     180
tgcgtatccg accatcctgt gacatttgga aaaatccatt gcgtcagagc atccagcggc     240
cacaaaacgg atctccaaat tggcgcggtc atccggacgg cagcgtttga tgacgaattt     300
tattatgacg gagagctggg cgccgtttat accgcggatc ataccgtatt taaagtatgg     360
gcgcctgctg caacctcagc tgctgtcaag cttttcacacc ccaataaaag cgggcgcaca     420
ttccaaatga ctcgcttgga aaaaggcgtc tatgccgtta cggtcacagg tgaccttcac     480
ggatatgagt atttgttttg catctgcaac aattcagaat ggatggaaac agttgaccag     540
tatgccaagg ctgtgactgt aaatggagag aagggcgtcg tcttgcgccc ggatcaaatg     600
aaatggactg ctcctcttaa accattctca caccctgtgg atgccgtcat ctatgagacg     660
catcttcgcg acttctccat ccatgaaaac agcggcatga taaacaaggg aaaatactta     720
gcgctgacgg aaactgatac acaaaccgca aatggcagtt cttcgggatt agcgtatgta     780
aaagagcttg tgtgacaca tgtggagctt ctgccggtga atgattttgc cggagttgat     840
gaagagaagc cgcttgatgc atacaattgg ggatataacc cgcttcattt ctttgccccg     900
gagggaagct atgcctcaaa tcctcatgat cctcaaacga gaaaaacaga gctgaaacaa     960
atgatcaata ccctgcatca gcacggtctg cgagtcattc tggatgttgt ttttaaccat    1020
gtgtataaga gggagaattc cccctttgaa agacagtgc ccggttattt tttccggcac    1080
gacgaatgtg ggatgccatc aaacggcacc ggcgttggca atgatattgc atcagaaaga    1140
```

```
aggatggcaa gaaaattcat tgcggattgc gtggtctatt ggcttgaaga atacaatgtt    1200
gacggcttcc gctttgatct cctcgggatt ttagatattg acaccgtgct ttatatgaaa    1260
gagaaagcaa ctaaggcaaa gcccggaatc ctgcttttg  gagaagggtg ggacctggct    1320
acaccgctgc cgcatgaaca gaaagctgct ttggcgaacg cgccaagaat gccgggcatc    1380 ggcttttta  atgatatgtt tcgtgacgct gtaaaaggga cacctttca  ccttaaggca    1440 acagggtttg cgctcggcaa cggtgaatca gcacaagctg tgatgcatgg aattgccggg    1500
tcttccggat ggaaggcatt agcaccgatt gttccggaac caagccagtc catcaattat    1560
gtcgaatcac acgacaatca cacctttggg gataaaatga gctttgcgct tcctcaagaa    1620
aatgacagcc gaaagcgaag caggcaaagg cttgcagtcg cgattatttt gcttgcccaa    1680
ggggtgccgt ttattcacag cggccaggaa ttttccgga  cgaagcaggg agtgaaaaac    1740
agctatcaat ccagtgacag catcaaccag ctcgactggg atcgccgtga acattcaaa    1800 gaagatgttc actatatccg caggctgatc tcgctgagaa aagcgcatcc tgcattccgt    1860
cttaggtccg ctgcagacat ccagcgccat cttgaatgct tgacgctaaa agaacacctt    1920
atcgcataca ggctttatga tcttgacgag gttgacgaat ggaaagatat cattgttatc    1980
catcacgcga gtccagactc cgtcgagtgg aggctgccaa cgacatacc  ttatcggctt    2040 ttatgtgatc catcaggatt tcaggaagac ccaacagaaa tcaagaaaac ggttgcagta    2100
aacggcatcg gaacggttat cttatattta gcatcagatc ttaagagttt tgcttgacga    2160
agtttgtgct atagcgctaa aatttaaagg acggctattg attagcatat gagactctca    2220
atagctgtct ttt                                                      2233

<210> SEQ ID NO 2
<211> LENGTH: 718
<212> TYPE: PRT
<213> ORGANISM: Bacillus subtilis

<400> SEQUENCE: 2

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Ile Thr Asp Phe Pro Leu Ala Val Arg
        35                  40                  45

Glu Glu Tyr Ser Leu Glu Ala Lys Tyr Lys Tyr Val Cys Val Ser Asp
    50                  55                  60

His Pro Val Thr Phe Gly Lys Ile His Cys Val Arg Ala Ser Ser Gly
65                  70                  75                  80

His Lys Thr Asp Leu Gln Ile Gly Ala Val Ile Arg Thr Ala Ala Phe
            85                  90                  95

Asp Asp Glu Phe Tyr Tyr Asp Gly Glu Leu Gly Ala Val Tyr Thr Ala
        100                 105                 110

Asp His Thr Val Phe Lys Val Trp Ala Pro Ala Ala Thr Ser Ala Ala
    115                 120                 125

Val Lys Leu Ser His Pro Asn Lys Ser Gly Arg Thr Phe Gln Met Thr
130                 135                 140

Arg Leu Glu Lys Gly Val Tyr Ala Val Thr Val Thr Gly Asp Leu His
145                 150                 155                 160

Gly Tyr Glu Tyr Leu Phe Cys Ile Cys Asn Asn Ser Glu Trp Met Glu
            165                 170                 175
```

-continued

```
Thr Val Asp Gln Tyr Ala Lys Ala Val Thr Val Asn Gly Glu Lys Gly
                180                 185                 190

Val Val Leu Arg Pro Asp Gln Met Lys Trp Thr Ala Pro Leu Lys Pro
            195                 200                 205

Phe Ser His Pro Val Asp Ala Val Ile Tyr Glu Thr His Leu Arg Asp
        210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Val Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr Lys Arg Glu Asn Ser Pro Phe Glu Lys Thr
            340                 345                 350

Val Pro Gly Tyr Phe Phe Arg His Asp Glu Cys Gly Met Pro Ser Asn
        355                 360                 365

Gly Thr Gly Val Gly Asn Asp Ile Ala Ser Glu Arg Arg Met Ala Arg
370                 375                 380

Lys Phe Ile Ala Asp Cys Val Val Tyr Trp Leu Glu Glu Tyr Asn Val
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Thr Lys Ala Lys Pro Gly Ile Leu Leu
            420                 425                 430

Phe Gly Glu Gly Trp Asp Leu Ala Thr Pro Leu Pro His Glu Gln Lys
        435                 440                 445

Ala Ala Leu Ala Asn Ala Pro Arg Met Pro Gly Ile Gly Phe Phe Asn
450                 455                 460

Asp Met Phe Arg Asp Ala Val Lys Gly Asn Thr Phe His Leu Lys Ala
465                 470                 475                 480

Thr Gly Phe Ala Leu Gly Asn Gly Glu Ser Ala Gln Ala Val Met His
                485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Ser Phe Ala Leu Pro Gln Glu Asn Asp Ser Arg
530                 535                 540

Lys Arg Ser Arg Gln Arg Leu Ala Val Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val His Tyr Ile Arg Arg
```

|     | 595 |     |     |     | 600 |     |     |     | 605 |     |     |
| --- | --- | --- | --- | --- | --- | --- | --- | --- | --- | --- | --- |

Leu Ile Ser Leu Arg Lys Ala His Pro Ala Phe Arg Leu Arg Ser Ala
610 615 620

Ala Asp Ile Gln Arg His Leu Glu Cys Leu Thr Leu Lys Glu His Leu
625 630 635 640

Ile Ala Tyr Arg Leu Tyr Asp Leu Asp Glu Val Asp Glu Trp Lys Asp
645 650 655

Ile Ile Val Ile His His Ala Ser Pro Asp Ser Val Glu Trp Arg Leu
660 665 670

Pro Asn Asp Ile Pro Tyr Arg Leu Leu Cys Asp Pro Ser Gly Phe Gln
675 680 685

Glu Asp Pro Thr Glu Ile Lys Lys Thr Val Ala Val Asn Gly Ile Gly
690 695 700

Thr Val Ile Leu Tyr Leu Ala Ser Asp Leu Lys Ser Phe Ala
705 710 715

<210> SEQ ID NO 3
<211> LENGTH: 30
<212> TYPE: DNA
<213> ORGANISM: Artificial
<220> FEATURE:
<223> OTHER INFORMATION: PCR primer

<400> SEQUENCE: 3
ggccatggtc agcatccgcc gcagcttcga                     30

<210> SEQ ID NO 4
<211> LENGTH: 30
<212> TYPE: DNA
<213> ORGANISM: Artificial
<220> FEATURE:
<223> OTHER INFORMATION: PCR primer

<400> SEQUENCE: 4
ggctcgagtc aagcaaaact cttaagatct                     30

<210> SEQ ID NO 5
<211> LENGTH: 33
<212> TYPE: DNA
<213> ORGANISM: Artificial
<220> FEATURE:
<223> OTHER INFORMATION: PCR primer

<400> SEQUENCE: 5
gtaaaaggga acaccggtca ccttaaggca ata                 33

<210> SEQ ID NO 6
<211> LENGTH: 33
<212> TYPE: DNA
<213> ORGANISM: Artificial
<220> FEATURE:
<223> OTHER INFORMATION: PCR primer

<400> SEQUENCE: 6
gtaaaaggga acacctctca ccttaaggca ata                 33

<210> SEQ ID NO 7
<211> LENGTH: 20
<212> TYPE: DNA
<213> ORGANISM: Artificial
<220> FEATURE:
<223> OTHER INFORMATION: PCR primer

```
<400> SEQUENCE: 7
ttattgccgg agagtggcga                                              20

<210> SEQ ID NO 8
<211> LENGTH: 20
<212> TYPE: DNA
<213> ORGANISM: Artificial
<220> FEATURE:
<223> OTHER INFORMATION: PCR primer

<400> SEQUENCE: 8
ccagactgct gacaaagtgc                                              20

<210> SEQ ID NO 9
<211> LENGTH: 34
<212> TYPE: DNA
<213> ORGANISM: Artificial
<220> FEATURE:
<223> OTHER INFORMATION: PCR primer

<400> SEQUENCE: 9
ggaattccat atggatgtcg tcgtccgctt accg                              34

<210> SEQ ID NO 10
<211> LENGTH: 29
<212> TYPE: DNA
<213> ORGANISM: Artificial
<220> FEATURE:
<223> OTHER INFORMATION: PCR primer

<400> SEQUENCE: 10
gctctagatt atttactgct caccggcag                                    29

<210> SEQ ID NO 11
<211> LENGTH: 19
<212> TYPE: DNA
<213> ORGANISM: Artificial
<220> FEATURE:
<223> OTHER INFORMATION: PCR primer

<400> SEQUENCE: 11
gccggccgac tccggtgac                                               19

<210> SEQ ID NO 12
<211> LENGTH: 3664
<212> TYPE: DNA
<213> ORGANISM: Klebsiella pneumoniae

<400> SEQUENCE: 12
tggcgataag cgtggcgaat cataatcagt ttgcggtttc gggtcgtcat tcccttatt    60 gatttactcc cccggcttcc tacgccccccc gctcatttgt gggggatgat tgcgcctggg  120
aaagcaaaaa tatctaatta gcgcgctgta aagatattca tcctttctta ccttttataa  180
tttaataagc atattaggga ctatcgaatg ctcagatata cctgtcatgc ctatttctt   240 ggatcgttag tattattgag tggctgtgat aacagctctt cctcttctac ctctggctca  300
ccgggttcac caggcaatcc tggcaaccca ggcactcccg gcacgcccga cccgcaggat  360
gtcgtcgtcc gcttaccgga cgttgccgtc ccaggcgaag cggtgcaggc ttccgccagg  420
caggctgtca ttcatctcgt cgatatcgcc ggcatcacca gcagcacgcc ggccgactat  480
gcgacgaaaa acctctattt atggaacaac gaaacctgtg acgcgctgag cgcgccggtg  540
gcggactgga atgatgtcag caccaccccg accggcagcg acaaatatgg cccttattgg  600
```

-continued

```
gtgatcccgc tgactaaaga gagcggatgc atcaacgtta tcgtccgcga tggcaccaat    660
aagcttatcg acagcgacct gcgcgtctct ttcagtgatt tcaccgatcg gacggtatcg    720
gtcatcgccg gcaacagcgc ggtctatgac tcccgcgccg acgccttccg cgccgccttt    780
ggcgtggcgc tggccgatgc gcactgggtc gataagacta ctctgctgtg gccgggtggg    840
gaaaataaac ccattgtgcg cctctattac agccacagca gtaaggtggc cgccgacagt    900
aacggcgaat ttagcgataa atatgtcaag ctgaccccca ccaccgtcag ccagcaggta    960
agcatgcgct ccccgcatct cgccagctat ccagcctttt aactgccgga tgatgttaac   1020
gtcgatgaat tgctgcaggg cgagacggtg gcgatagccg cggaaagcga tgggatcctg   1080
agctcagcca cccaggtgca gaccgccggc gtgctggacg ataccctatg cgccgccgcc   1140
gaggcgctga gctatggcgc ccagctaacc gatagcggcg tgaccttccg cgtctgggcg   1200
cccacggcgc agcaggtcga gctggtgatc tatagcgcgg acaagaaagt gatagccagt   1260
cacccgatga cccgcgatag cgcctccggc gcctggtcct ggcaggggggg aagcgacctg   1320
aagggcgcct tctaccgcta cgcgatgacg gtctaccacc cgcagtcgcg taaagtcgag   1380
cagtacgaag tgaccgatcc ctacgcccac agtttgtcga ccaactcgga gtacagccag   1440
gtggtcgatc tcaacgacag cgcgctgaag ccggaaggct gggacgggct gacgatgccg   1500
cacgcgcaga aaaccaaagc cgatctggcg aaaatgacga ttcacgaatc gcatattcgc   1560
gatctctccg cctgggatca aaccgtgcct gcggagctgc gcggtaagta tctggcgctc   1620
accgcccagg aaagcaatat ggtccagcat ctgaaacagc tgtcggcctc gggcgtgacc   1680
catattgagc tgctgccggt cttcgatctg gcgacggtca atgagttcag cgacaaggtc   1740
gccgatattc agcagccgtt cagccgcctg tgcgaggtca atagcgcggt gaagagcagc   1800
gagttcgcgg gctattgcga cagcggttcg acggtcgaag aggtgctgac ccagctgaag   1860
cagaacgaca gcaaggataa cccgcaggtg caggcgttga atacgctggt ggcgcagacc   1920
gactcctata actggggcta cgatccgttc cactacacgg taccggaagg atcctacgcc   1980
accgatccgg aaggcacggc gcgtattaaa gagttccgca ccatgattca ggcgatcaag   2040
caggatctgg gaatgaacgt cattatggac gtggtgtaca accacaccaa cgccgccggc   2100
ccgaccgatc gcacctcggt actggataag atcgtcccct ggtactacca gcgtctgaac   2160
gaaaccaccg gcagcgtgga atcggctacc tgttgctccg actcggcgcc agagcaccgg   2220
atgttcgcca agcttatcgc cgattcactg gcggtatgga ccaccgatta taagatcgat   2280
ggcttccgct tcgacctgat gggctaccac ccgaaagcgc agatcctctc ggcctgggaa   2340
cgcattaaag cgctgaaccc ggatatctac ttctttggcg aaggctggga ttccaaccag   2400
agcgatcgct ttgaaattgc ctcgcaaatc aatctcaaag caccgggat cggcacgttc   2460
tccgatcgtc tgcgcgacgc cgtgcgcggc ggcgggccgt tcgactccgg tgacgcatta   2520
cgccagaacc agggcgtggg cagcggggct ggcgttctgc cgaatgagct gaccaccctg   2580
agcgacgatc aggcgcgtca cctcgccgat ctgacccgtc tcggcatggc cggtaacctt   2640
gcggactttg tgctgatcga caaagacggc gcggtgaaga gaggcagcga gattgattat   2700
aacgcgcgc caggcggcta tgcggctgat ccgacgaag tcgtgaacta tgtgtcaaaa   2760
cacgataacc agacgctgtg gacatgatc agctataaag ccgctcagga ggcggatctc   2820
gatacccgcg tccggatgca ggcggtgtcg ctggcgacgg tgatgctcgg ccaagggatc   2880
gcctttgacc agcagggctc ggagctgctg cgctctaaat cctttacccg cgattcgtat   2940
```

-continued

```
gattccggcg actggtttaa ccgcgtggac tactccctgc aggacaacaa ctacaacgtc    3000
ggtatgccgc gcagcagcga tgatggcagc aattatgaca ttatcgcccg ggtgaaagac    3060
gcggtggcta ctccgggtga acggagctc aagcagatga ccgcgtttta tcaggagctg     3120
accgcgctgc gtaaatcgtc tccgctgttt accctcggcg acggcgcgac ggtgatgaag    3180
cgcgtggact tccgcaatac tggcgccgat cagcagacgg tctgctggt gatgaccatc     3240
gatgacggga tgcaggctgg cgccagtctg acagccgtg tcgacggcat cgtggtggcg     3300
atcaacgccg cgccggaaag ccggacgctg caggacttcg ccggcacatc gctccagctg    3360
agcgctattc agcaggcggc gggcgaccgg tcgctggcga cggcgtgca ggttgccgct     3420
gacggttcgg tcacgctgcc ggcctggtcg gttgccgttc tcgagttgcc gcagggcgag    3480
tcgcagggcg ctggcctgcc ggtgagcagt aaataacata acgtagggcg cccgtaaggg    3540
cgcctctggc tgatgacaaa cctgtttcgt tattgtgctc gcctttctgt cgggtggcgg    3600
ctttcgctta cccggcctac gaaagattgc aatttcaaac agttatgcag ttatctgtag    3660
gccc                                                                 3664
```

<210> SEQ ID NO 13
<211> LENGTH: 1083
<212> TYPE: PRT
<213> ORGANISM: Klebsiella pneumoniae

<400> SEQUENCE: 13

```
Cys Asp Asn Ser Ser Ser Ser Thr Ser Gly Ser Pro Gly Ser Pro
  1               5                  10                  15

Gly Asn Pro Gly Asn Pro Gly Thr Pro Gly Thr Pro Asp Pro Gln Asp
             20                  25                  30

Val Val Arg Leu Pro Asp Val Ala Val Pro Gly Glu Ala Val Gln
         35                  40                  45

Ala Ser Ala Arg Gln Ala Val Ile His Leu Val Asp Ile Ala Gly Ile
     50                  55                  60

Thr Ser Ser Thr Pro Ala Asp Tyr Ala Thr Lys Asn Leu Tyr Leu Trp
 65                  70                  75                  80

Asn Asn Glu Thr Cys Asp Ala Leu Ser Ala Pro Val Ala Asp Trp Asn
                 85                  90                  95

Asp Val Ser Thr Thr Pro Thr Gly Ser Asp Lys Tyr Gly Pro Tyr Trp
            100                 105                 110

Val Ile Pro Leu Thr Lys Glu Ser Gly Cys Ile Asn Val Ile Val Arg
        115                 120                 125

Asp Gly Thr Asn Lys Leu Ile Asp Ser Asp Leu Arg Val Ser Phe Ser
    130                 135                 140

Asp Phe Thr Asp Arg Thr Val Ser Val Ile Ala Gly Asn Ser Ala Val
145                 150                 155                 160

Tyr Asp Ser Arg Ala Asp Ala Phe Arg Ala Ala Phe Gly Val Ala Leu
                165                 170                 175

Ala Asp Ala His Trp Val Asp Lys Thr Thr Leu Leu Trp Pro Gly Gly
            180                 185                 190

Glu Asn Lys Pro Ile Val Arg Leu Tyr Tyr Ser His Ser Ser Lys Val
        195                 200                 205

Ala Ala Asp Ser Asn Gly Glu Phe Ser Asp Lys Tyr Val Lys Leu Thr
    210                 215                 220

Pro Thr Thr Val Ser Gln Gln Val Ser Met Arg Phe Pro His Leu Ala
225                 230                 235                 240
```

-continued

```
Ser Tyr Pro Ala Phe Lys Leu Pro Asp Asp Val Asn Val Asp Glu Leu
                245                 250                 255

Leu Gln Gly Glu Thr Val Ala Ile Ala Ala Glu Ser Asp Gly Ile Leu
            260                 265                 270

Ser Ser Ala Thr Gln Val Gln Thr Ala Gly Val Leu Asp Asp Thr Tyr
        275                 280                 285

Ala Ala Ala Ala Glu Ala Leu Ser Tyr Gly Ala Gln Leu Thr Asp Ser
    290                 295                 300

Gly Val Thr Phe Arg Val Trp Ala Pro Thr Ala Gln Gln Val Glu Leu
305                 310                 315                 320

Val Ile Tyr Ser Ala Asp Lys Lys Val Ile Ala Ser His Pro Met Thr
                325                 330                 335

Arg Asp Ser Ala Ser Gly Ala Trp Ser Trp Gln Gly Gly Ser Asp Leu
            340                 345                 350

Lys Gly Ala Phe Tyr Arg Tyr Ala Met Thr Val Tyr His Pro Gln Ser
        355                 360                 365

Arg Lys Val Glu Gln Tyr Glu Val Thr Asp Pro Tyr Ala His Ser Leu
    370                 375                 380

Ser Thr Asn Ser Glu Tyr Ser Gln Val Val Asp Leu Asn Asp Ser Ala
385                 390                 395                 400

Leu Lys Pro Glu Gly Trp Asp Gly Leu Thr Met Pro His Ala Gln Lys
                405                 410                 415

Thr Lys Ala Asp Leu Ala Lys Met Thr Ile His Glu Ser His Ile Arg
            420                 425                 430

Asp Leu Ser Ala Trp Asp Gln Thr Val Pro Ala Glu Leu Arg Gly Lys
        435                 440                 445

Tyr Leu Ala Leu Thr Ala Gln Glu Ser Asn Met Val Gln His Leu Lys
    450                 455                 460

Gln Leu Ser Ala Ser Gly Val Thr His Ile Glu Leu Leu Pro Val Phe
465                 470                 475                 480

Asp Leu Ala Thr Val Asn Glu Phe Ser Asp Lys Val Ala Asp Ile Gln
                485                 490                 495

Gln Pro Phe Ser Arg Leu Cys Glu Val Asn Ser Ala Val Lys Ser Ser
            500                 505                 510

Glu Phe Ala Gly Tyr Cys Asp Ser Gly Ser Thr Val Glu Glu Val Leu
        515                 520                 525

Thr Gln Leu Lys Gln Asn Asp Ser Lys Asp Asn Pro Gln Val Gln Ala
    530                 535                 540

Leu Asn Thr Leu Val Ala Gln Thr Asp Ser Tyr Asn Trp Gly Tyr Asp
545                 550                 555                 560

Pro Phe His Tyr Thr Val Pro Glu Gly Ser Tyr Ala Thr Asp Pro Glu
                565                 570                 575

Gly Thr Ala Arg Ile Lys Glu Phe Arg Thr Met Ile Gln Ala Ile Lys
            580                 585                 590

Gln Asp Leu Gly Met Asn Val Ile Met Asp Val Val Tyr Asn His Thr
        595                 600                 605

Asn Ala Ala Gly Pro Thr Asp Arg Thr Ser Val Leu Asp Lys Ile Val
    610                 615                 620

Pro Trp Tyr Tyr Gln Arg Leu Asn Glu Thr Thr Gly Ser Val Glu Ser
625                 630                 635                 640

Ala Thr Cys Cys Ser Asp Ser Ala Pro Glu His Arg Met Phe Ala Lys
                645                 650                 655

Leu Ile Ala Asp Ser Leu Ala Val Trp Thr Thr Asp Tyr Lys Ile Asp
```

660             665              670
Gly Phe Arg Phe Asp Leu Met Gly Tyr His Pro Lys Ala Gln Ile Leu
            675             680              685

Ser Ala Trp Glu Arg Ile Lys Ala Leu Asn Pro Asp Ile Tyr Phe Phe
    690             695             700

Gly Glu Gly Trp Asp Ser Asn Gln Ser Asp Arg Phe Glu Ile Ala Ser
705             710             715                 720

Gln Ile Asn Leu Lys Gly Thr Gly Ile Gly Thr Phe Ser Asp Arg Leu
                725             730              735

Arg Asp Ala Val Arg Gly Gly Pro Phe Asp Ser Gly Asp Ala Leu
            740             745             750

Arg Gln Asn Gln Gly Val Gly Ser Gly Ala Gly Val Leu Pro Asn Glu
        755             760             765

Leu Thr Thr Leu Ser Asp Asp Gln Ala Arg His Leu Ala Asp Leu Thr
    770             775             780

Arg Leu Gly Met Ala Gly Asn Leu Ala Asp Phe Val Leu Ile Asp Lys
785             790             795             800

Asp Gly Ala Val Lys Arg Gly Ser Glu Ile Asp Tyr Asn Gly Ala Pro
                805             810              815

Gly Gly Tyr Ala Ala Asp Pro Thr Glu Val Val Asn Tyr Val Ser Lys
            820             825             830

His Asp Asn Gln Thr Leu Trp Asp Met Ile Ser Tyr Lys Ala Ala Gln
        835             840             845

Glu Ala Asp Leu Asp Thr Arg Val Arg Met Gln Ala Val Ser Leu Ala
    850             855             860

Thr Val Met Leu Gly Gln Gly Ile Ala Phe Asp Gln Gln Gly Ser Glu
865             870             875             880

Leu Leu Arg Ser Lys Ser Phe Thr Arg Asp Ser Tyr Asp Ser Gly Asp
                885             890             895

Trp Phe Asn Arg Val Asp Tyr Ser Leu Gln Asp Asn Asn Tyr Asn Val
            900             905             910

Gly Met Pro Arg Ser Ser Asp Asp Gly Ser Asn Tyr Asp Ile Ile Ala
        915             920             925

Arg Val Lys Asp Ala Val Ala Thr Pro Gly Glu Thr Glu Leu Lys Gln
    930             935             940

Met Thr Ala Phe Tyr Gln Glu Leu Thr Ala Leu Arg Lys Ser Ser Pro
945             950             955             960

Leu Phe Thr Leu Gly Asp Gly Ala Thr Val Met Lys Arg Val Asp Phe
                965             970             975

Arg Asn Thr Gly Ala Asp Gln Gln Thr Gly Leu Leu Val Met Thr Ile
            980             985             990

Asp Asp Gly Met Gln Ala Gly Ala Ser Leu Asp Ser Arg Val Asp Gly
        995             1000            1005

Ile Val Val Ala Ile Asn Ala Ala Pro Glu Ser Arg Thr Leu Gln
    1010            1015            1020

Asp Phe Ala Gly Thr Ser Leu Gln Leu Ser Ala Ile Gln Gln Ala
    1025            1030            1035

Ala Gly Asp Arg Ser Leu Ala Ser Gly Val Gln Val Ala Ala Asp
    1040            1045            1050

Gly Ser Val Thr Leu Pro Ala Trp Ser Val Ala Val Leu Glu Leu
    1055            1060            1065

Pro Gln Gly Glu Ser Gln Gly Ala Gly Leu Pro Val Ser Ser Lys
    1070            1075            1080

<210> SEQ ID NO 14
<211> LENGTH: 922
<212> TYPE: PRT
<213> ORGANISM: Bacillus sp.

<400> SEQUENCE: 14

```
Asp Gly Thr Thr Thr Asn Val Ile Val His Tyr Phe Arg Pro Gly Gly
1               5                   10                  15

Asp Tyr Gln Ser Trp Ser Leu Trp Met Trp Pro Glu Gly Gly Asp Gly
            20                  25                  30

Asn Asn Tyr Asn Phe Asn Gly Thr Asp Ser Tyr Gly Glu Ile Ala Asn
        35                  40                  45

Val Ser Ile Pro Gly Ser Pro Ser Lys Val Gly Ile Val Arg Thr
    50                  55                  60

Gln Asp Trp Ala Lys Asp Val Ser Gln Asp Arg Tyr Ile Asp Leu Ser
65                  70                  75                  80

Lys Gly His Glu Val Trp Leu Val Gln Gly Asn Ser Gln Ile Phe Tyr
                85                  90                  95

Asn Glu Lys Asp Ala Glu Asp Ala Ala Glu Pro Ala Val Ser Asn Ala
            100                 105                 110

Tyr Leu Asp Ala Pro Asn Lys Val Leu Val Lys Leu Ser Gln Pro Phe
        115                 120                 125

Thr Leu Gly Glu Gly Ala Ser Gly Phe Thr Val His Asp Asp Thr Ala
    130                 135                 140

Asn Gly Asp Ile Pro Val Thr Lys Val Lys Asn Ala Asn Lys Val Glu
145                 150                 155                 160

Asp Val Thr Ala Ile Leu Ala Gly Thr Phe Gln His Ile Phe Gly Gly
                165                 170                 175

Ser Asp Trp Ala Pro Asp Asn His Ser Thr Gln Leu Lys Lys Val Asn
            180                 185                 190

Asp Asn Leu Tyr Gln Phe Ser Gly Glu Leu Pro Gly Gly Ser Tyr Gln
        195                 200                 205

Tyr Lys Val Ala Leu Asn Asp Ser Trp Asn Ser Ser Tyr Pro Ser Asp
    210                 215                 220

Asn Ile Asn Leu Thr Val Pro Asp Gly Gly Ala His Val Thr Phe Ser
225                 230                 235                 240

Tyr Val Pro Ser Thr His Ala Val Tyr Asp Thr Ile Asn Asn Pro Gly
                245                 250                 255

Ala Asn Leu Pro Leu Asp Gly Ser Gly Ile Lys Thr Asp Leu Val Thr
            260                 265                 270

Val Thr Leu Gly Glu Asn Pro Asp Val Ser His Thr Leu Ser Ile Gln
        275                 280                 285

Thr Asp Gly Phe Lys Thr Gly Arg Val Ile Pro Arg Asn Val Leu Asp
    290                 295                 300

Phe Ser Gln Tyr Tyr Ser Gly Glu Asp Leu Gly Asn Thr Tyr Thr
305                 310                 315                 320

Lys Lys Ala Thr Thr Phe Lys Val Trp Ala Pro Thr Ser Thr Lys Val
                325                 330                 335

Asn Val Leu Leu Tyr Asn Lys Ala Ala Gly Ala Leu Thr Lys Thr Val
            340                 345                 350

Pro Met Lys Ala Ser Gly His Gly Val Trp Ser Val Thr Val Pro Gln
        355                 360                 365

Asn Leu Glu Asn Trp Tyr Tyr Leu Tyr Glu Val Thr Gly Gln Gly Ser
```

-continued

```
                370                 375                 380
Thr Arg Thr Ala Val Asp Pro Tyr Ala Thr Ala Ile Ala Pro Asn Gly
385                 390                 395                 400

Thr Arg Gly Met Val Val Asp Leu Ala Lys Thr Asn Pro Thr Gly Trp
                405                 410                 415

Lys Ser Asp Lys His Met Thr Pro Lys Asn Ile Glu Asp Glu Val Ile
                420                 425                 430

Tyr Glu Met His Val Arg Asp Phe Ser Ile Asp Ser Asn Ser Gly Met
                435                 440                 445

Thr Asn Lys Gly Lys Tyr Leu Ala Leu Thr Glu Lys Gly Thr Lys Gly
                450                 455                 460

Pro Glu Asn Val Lys Thr Gly Val Asp Ser Leu Lys Gln Leu Gly Ile
465                 470                 475                 480

Thr His Val Gln Leu Gln Pro Val Phe Ala Phe Asn Ser Val Asp Glu
                485                 490                 495

Thr Asp Pro Thr Gln Tyr Asn Trp Gly Tyr Asp Pro Arg Asn Tyr Asn
                500                 505                 510

Val Pro Glu Gly Gln Tyr Ala Thr Asp Ala Asn Gly Thr Thr Arg Ile
                515                 520                 525

Lys Glu Phe Lys Glu Met Val Leu Ser Leu His Arg Asn His Ile Gly
530                 535                 540

Val Asn Met Asp Val Val Tyr Asn His Thr Phe Ala Thr Gln Ile Ser
545                 550                 555                 560

Asp Phe Asp Lys Ile Val Pro Gln Tyr Tyr Tyr Arg Thr Asp Asp Ala
                565                 570                 575

Gly Asn Tyr Thr Asn Gly Ser Gly Thr Gly Asn Glu Val Ala Ala Glu
                580                 585                 590

Arg Pro Met Val Gln Lys Phe Ile Ile Asp Ser Leu Lys Tyr Trp Val
                595                 600                 605

Asn Glu Tyr His Ile Asp Gly Phe Arg Phe Asp Leu Met Ala Leu Leu
                610                 615                 620

Gly Lys Asp Thr Met Ala Lys Ala Ala Gln Glu Leu His Ala Ile Asp
625                 630                 635                 640

Pro Gly Ile Ala Leu Tyr Gly Glu Pro Trp Thr Gly Thr Ser Ala
                645                 650                 655

Leu Pro Thr Asp Gln Leu Leu Thr Lys Gly Val Gln Lys Gly Met Gly
                660                 665                 670

Val Ala Val Phe Asn Asp Asn Leu Arg Asn Gly Leu Asp Gly Asn Val
                675                 680                 685

Phe Asp Ala Ser Ser Gln Gly Phe Ala Thr Gly Ala Thr Gly Leu Thr
690                 695                 700

Asp Val Ile Lys Lys Gly Val Glu Gly Ser Ile Asn Asp Phe Thr Ser
705                 710                 715                 720

Ser Pro Gly Glu Thr Ile Asn Tyr Val Thr Ser His Asp Asn Tyr Thr
                725                 730                 735

Leu Trp Asp Lys Ile Ala Gln Ser Asn Pro Asn Asp Ser Glu Ala Asp
                740                 745                 750

Arg Ile Lys Met Asp Glu Leu Ala Gln Ala Val Val Thr Ser Gln
                755                 760                 765

Gly Val Pro Phe Met Gln Gly Gly Glu Glu Met Leu Arg Thr Lys Gly
                770                 775                 780

Gly Asn Ser Asn Ser Tyr Asn Ala Gly Asp Ala Val Asn Glu Phe Asp
785                 790                 795                 800
```

```
Trp Ser Arg Lys Ala Gln Tyr Ser Asp Val Phe Asn Tyr Tyr Ser Gly
            805                 810                 815

Leu Ile His Leu Arg Leu Ala His Pro Ala Phe Arg Met Thr Thr Ala
            820                 825                 830

Asn Gln Ile Lys Glu His Leu Gln Phe Ile Asp Ser Pro Asp Asn Thr
            835                 840                 845

Val Ala Tyr Glu Leu Thr Asn His Ala Asn Lys Asp Lys Trp Gly Asn
            850                 855                 860

Ile Val Val Ile Tyr Asn Pro Asn Lys Thr Ala Glu Thr Val Asn Leu
865                 870                 875                 880

Pro Ser Gly Lys Trp Ala Ile Asn Ala Thr Asn Gly Lys Ile Gly Glu
            885                 890                 895

Ser Thr Leu Ser His Ala Glu Gly His Val Gln Val Pro Gly Ile Ser
            900                 905                 910

Met Met Ile Leu His Gln Glu Thr Asn Lys
            915                 920

<210> SEQ ID NO 15
<211> LENGTH: 928
<212> TYPE: PRT
<213> ORGANISM: Bacillus deramificans

<400> SEQUENCE: 15

Asp Gly Asn Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly Gly
                20                  25                  30

Ala Glu Tyr Asp Phe Asn Gln Pro Ala Asp Ser Phe Gly Ala Val Ala
            35                  40                  45

Ser Ala Asp Ile Pro Gly Asn Pro Ser Gln Val Gly Ile Ile Val Arg
        50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
                85                  90                  95

Tyr Asn Glu Lys Asp Ala Glu Asp Ala Ala Lys Pro Ala Val Ser Asn
            100                 105                 110

Ala Tyr Leu Asp Ala Ser Asn Gln Val Leu Val Lys Leu Ser Gln Pro
        115                 120                 125

Leu Thr Leu Gly Glu Gly Ala Ser Gly Phe Thr Val His Asp Asp Thr
130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
            165                 170                 175

Gly Ser Asp Trp Ala Pro Asp Asn His Ser Thr Leu Leu Lys Lys Val
        180                 185                 190

Thr Asn Asn Leu Tyr Gln Phe Ser Gly Asp Leu Pro Glu Gly Asn Tyr
            195                 200                 205

Gln Tyr Lys Val Ala Leu Asn Asp Ser Trp Asn Asn Pro Ser Tyr Pro
        210                 215                 220

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
```

```
            245                 250                 255
Pro Asn Ala Asp Leu Gln Val Glu Ser Gly Val Lys Thr Asp Leu Val
            260                 265                 270

Thr Val Thr Leu Gly Glu Asp Pro Val Ser His Thr Leu Ser Ile
        275                 280                 285

Gln Thr Asp Gly Tyr Gln Ala Lys Gln Val Ile Pro Arg Asn Val Leu
    290                 295                 300

Asn Ser Ser Gln Tyr Tyr Tyr Ser Gly Asp Asp Leu Gly Asn Thr Tyr
305                 310                 315                 320

Thr Gln Lys Ala Thr Thr Phe Lys Val Trp Ala Pro Thr Ser Thr Gln
                325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
        355                 360                 365

Gln Asn Leu Glu Asn Trp Tyr Tyr Met Tyr Glu Val Thr Gly Gln Gly
    370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
        435                 440                 445

Met Lys Asn Lys Gly Lys Tyr Leu Ala Leu Thr Glu Lys Gly Thr Lys
    450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
        515                 520                 525

Ile Lys Glu Phe Lys Glu Met Val Leu Ser Leu His Arg Glu His Ile
    530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
    610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Asp Asp Gln Leu Leu Thr Lys Gly Ala Gln Lys Gly Met
            660                 665                 670
```

```
Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
    690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
                725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
850                 855                 860

Asn Ile Ile Val Val Tyr Asn Pro Asn Lys Thr Val Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
            915                 920                 925

<210> SEQ ID NO 16
<211> LENGTH: 750
<212> TYPE: PRT
<213> ORGANISM: Pseudomonas amyloderamosa

<400> SEQUENCE: 16

Ala Ile Asn Ser Met Ser Leu Gly Ala Ser Tyr Asp Ala Gln Gln Ala
1               5                   10                  15

Asn Ile Thr Phe Arg Val Tyr Ser Ser Gln Ala Thr Arg Ile Val Leu
            20                  25                  30

Tyr Leu Tyr Ser Ala Gly Tyr Gly Val Gln Glu Ser Ala Thr Tyr Thr
        35                  40                  45

Leu Ser Pro Ala Gly Ser Gly Val Trp Ala Val Thr Val Pro Val Ser
    50                  55                  60

Ser Ile Lys Ala Ala Gly Ile Thr Gly Ala Val Tyr Tyr Gly Tyr Arg
65                  70                  75                  80

Ala Trp Gly Pro Asn Trp Pro Tyr Ala Ser Asn Trp Gly Lys Gly Ser
                85                  90                  95

Gln Ala Gly Phe Val Ser Asp Val Asp Ala Asn Gly Asp Arg Phe Asn
            100                 105                 110

Pro Asn Lys Leu Leu Leu Asp Pro Tyr Ala Gln Glu Val Ser Gln Asp
```

```
            115                 120                 125
Pro Leu Asn Pro Ser Asn Gln Asn Gly Asn Val Phe Ala Ser Gly Ala
130                 135                 140

Ser Tyr Arg Thr Thr Asp Ser Gly Ile Tyr Ala Pro Lys Gly Val Val
145                 150                 155                 160

Leu Val Pro Ser Thr Gln Ser Thr Gly Thr Lys Pro Thr Arg Ala Gln
                165                 170                 175

Lys Asp Asp Val Ile Tyr Glu Val His Val Arg Gly Phe Thr Glu Gln
                180                 185                 190

Asp Thr Ser Ile Pro Ala Gln Tyr Arg Gly Thr Tyr Tyr Gly Ala Gly
                195                 200                 205

Leu Lys Ala Ser Tyr Leu Ala Ser Leu Gly Val Thr Ala Val Glu Phe
210                 215                 220

Leu Pro Val Gln Glu Thr Gln Asn Asp Ala Asn Asp Val Val Pro Asn
225                 230                 235                 240

Ser Asp Ala Asn Gln Asn Tyr Trp Gly Tyr Met Thr Glu Asn Tyr Phe
                245                 250                 255

Ser Pro Asp Arg Arg Tyr Ala Tyr Asn Lys Ala Ala Gly Gly Pro Thr
                260                 265                 270

Ala Glu Phe Gln Ala Met Val Gln Ala Phe His Asn Ala Gly Ile Lys
                275                 280                 285

Val Tyr Met Asp Val Val Tyr Asn His Thr Ala Glu Gly Gly Thr Trp
290                 295                 300

Thr Ser Ser Asp Pro Thr Thr Ala Thr Ile Tyr Ser Trp Arg Gly Leu
305                 310                 315                 320

Asp Asn Ala Thr Tyr Tyr Glu Leu Thr Ser Gly Asn Gln Tyr Phe Tyr
                325                 330                 335

Asp Asn Thr Gly Ile Gly Ala Asn Phe Asn Thr Tyr Asn Thr Val Ala
                340                 345                 350

Gln Asn Leu Ile Val Asp Ser Leu Ala Tyr Trp Ala Asn Thr Met Gly
                355                 360                 365

Val Asp Gly Phe Arg Phe Asp Leu Ala Ser Val Leu Gly Asn Ser Cys
370                 375                 380

Leu Asn Gly Ala Tyr Thr Ala Ser Ala Pro Asn Cys Pro Asn Gly Gly
385                 390                 395                 400

Tyr Asn Phe Asp Ala Ala Asp Ser Asn Val Ala Ile Asn Arg Ile Leu
                405                 410                 415

Arg Glu Phe Thr Val Arg Pro Ala Ala Gly Gly Ser Gly Leu Asp Leu
                420                 425                 430

Phe Ala Glu Pro Trp Ala Ile Gly Gly Asn Ser Tyr Gln Leu Gly Gly
                435                 440                 445

Phe Pro Gln Gly Trp Ser Glu Trp Asn Gly Leu Phe Arg Asp Ser Leu
                450                 455                 460

Arg Gln Ala Gln Asn Glu Leu Gly Ser Met Thr Ile Tyr Val Thr Gln
465                 470                 475                 480

Asp Ala Asn Asp Phe Ser Gly Ser Ser Asn Leu Phe Gln Ser Ser Gly
                485                 490                 495

Arg Ser Pro Trp Asn Ser Ile Asn Phe Ile Asp Val His Asp Gly Met
                500                 505                 510

Thr Leu Lys Asp Val Tyr Ser Cys Asn Gly Ala Asn Asn Ser Gln Ala
                515                 520                 525

Trp Pro Tyr Gly Pro Ser Asp Gly Gly Thr Ser Thr Asn Tyr Ser Trp
530                 535                 540
```

```
Asp Gln Gly Met Ser Ala Gly Thr Gly Ala Ala Val Asp Gln Arg Arg
545                 550                 555                 560

Ala Ala Arg Thr Gly Met Ala Phe Glu Met Leu Ser Ala Gly Thr Pro
            565                 570                 575

Leu Met Gln Gly Gly Asp Glu Tyr Leu Arg Thr Leu Gln Cys Asn Asn
        580                 585                 590

Asn Ala Tyr Asn Leu Asp Ser Ser Ala Asn Trp Leu Thr Tyr Ser Trp
    595                 600                 605

Thr Thr Asp Gln Ser Asn Phe Tyr Thr Phe Ala Gln Arg Leu Ile Ala
610                 615                 620

Phe Arg Lys Ala His Pro Ala Leu Arg Pro Ser Ser Trp Tyr Ser Gly
625                 630                 635                 640

Ser Gln Leu Thr Trp Tyr Gln Pro Ser Gly Ala Val Ala Asp Ser Asn
            645                 650                 655

Tyr Trp Asn Asn Thr Ser Asn Tyr Ala Ile Tyr Ala Ile Asn Gly
        660                 665                 670

Pro Ser Leu Gly Asp Ser Asn Ser Ile Tyr Val Ala Tyr Asn Gly Trp
        675                 680                 685

Ser Ser Ser Val Thr Phe Thr Leu Pro Ala Pro Pro Ser Gly Thr Gln
            690                 695                 700

Trp Tyr Arg Val Thr Asp Thr Cys Asp Trp Asn Asp Gly Ala Ser Thr
705                 710                 715                 720

Phe Val Ala Pro Gly Ser Glu Thr Leu Ile Gly Ala Gly Thr Thr
                725                 730                 735

Tyr Gly Gln Cys Gly Gln Ser Leu Leu Leu Ile Ser Lys
            740                 745                 750

<210> SEQ ID NO 17
<211> LENGTH: 710
<212> TYPE: PRT
<213> ORGANISM: Bacillus licheniformis

<400> SEQUENCE: 17

Met Pro Gly Ile Ser Arg Pro Phe Glu Ala Tyr Leu Asp Glu Met Arg
1               5                   10                  15

Thr Ile Thr Val Leu Val Pro Lys Ser Arg Ala Ser Ser Cys Ser Pro
            20                  25                  30

Pro Phe Leu Leu Glu Asp Asp Gln Gly Glu Arg Ile Glu Leu Ser Val
        35                  40                  45

Lys Ala Gln Val Glu Leu Glu Glu Gln Phe Lys Tyr Val Leu Glu Ser
    50                  55                  60

Ser Cys Thr Val Pro Phe Gly Arg Val His Lys Val Cys Cys Glu Glu
65                  70                  75                  80

Ser Val Trp Thr Asp Leu Gln Ile Gly Ser Val Thr Arg Ser Ala Ala
            85                  90                  95

Phe Asp Lys Ala Phe Phe Tyr Asp Gly Arg Leu Gly Ala Phe Tyr Ser
        100                 105                 110

Lys Gly Ser Thr Leu Phe Lys Val Trp Ala Pro Thr Ala Ser Ala Ala
    115                 120                 125

Ala Ile Lys Leu Glu Asp Pro Asp Ser Leu Gln Thr Asn Thr Phe Gln
130                 135                 140

Met Met Arg Arg Lys Lys Gly Val Phe Glu Val Thr Val Glu Gly Asp
145                 150                 155                 160

Leu Asn Gly Trp Ser Tyr Leu Tyr Glu Leu Tyr Val Asn Gly Lys Pro
```

-continued

```
                165                 170                 175
Leu Leu Thr Val Asp Pro Tyr Ala Lys Ala Val Thr Ala Asn Gly Glu
            180                 185                 190

Lys Gly Val Val Leu Asp Pro Glu Glu Val Lys Val Glu Lys His Arg
        195                 200                 205

Ala Pro Arg Leu His Ser Pro Cys Asp Ala Val Ile Tyr Glu Val His
    210                 215                 220

Ile Arg Asp Phe Ser Ile His Glu Asp Ser Gly Met Arg His Lys Gly
225                 230                 235                 240

Lys Tyr Val Ala Phe Thr Glu Asp Gly Thr Glu Thr Ser Gly Gly Phe
                245                 250                 255

Ser Thr Gly Ile Ala Tyr Leu Lys Glu Leu Gly Val Thr His Ile Glu
            260                 265                 270

Val Leu Pro Phe His Asp Phe Ala Gly Val Asp Glu Leu Ser Pro Asp
        275                 280                 285

Gln Ser Tyr Asn Trp Gly Tyr Asn Pro Leu His Phe Asn Ala Pro Glu
    290                 295                 300

Gly Ser Tyr Ser Leu Asp Pro Gln Asn Pro Lys Cys Arg Ile Thr Glu
305                 310                 315                 320

Leu Lys Thr Met Ile Gln Ser Leu His Lys His Gly Phe Ser Val Ile
                325                 330                 335

Met Asp Ala Val Tyr Asn His Val Tyr Lys Arg Glu Thr Ser Pro Phe
            340                 345                 350

Glu Lys Thr Val Pro Gly Tyr Phe Phe Arg His Asn Glu Tyr Gly Phe
        355                 360                 365

Pro Ser Asp Gly Thr Gly Val Gly Asn Asp Ile Ala Ser Glu Arg Leu
    370                 375                 380

Met Val Arg Lys Tyr Ile Leu Asp Ser Val Arg Tyr Trp Leu Glu Glu
385                 390                 395                 400

Tyr Asp Val Asp Gly Ile Arg Phe Asp Leu Met Gly Ile Leu Asp Ile
                405                 410                 415

Glu Thr Val Arg Gln Ile Ser Thr Leu Ala Glu Asn Val Lys Pro Gly
            420                 425                 430

Val Leu Leu Phe Gly Glu Gly Trp Asp Leu Asn Thr Pro Leu Asp Ser
        435                 440                 445

Gly Gln Lys Ala Thr Leu Gln Asn Ala Gly Lys Val Pro Ala Val Gly
    450                 455                 460

Phe Phe Asn Asp Arg Phe Arg Asn Ala Val Lys Gly Ser Thr Phe Glu
465                 470                 475                 480

Leu Ser Asp Arg Gly Tyr Ala Leu Gly Asp Thr Gly Lys Lys Ala Ala
                485                 490                 495

Leu Gln His Gly Ile Ala Gly Ser Pro Gly Phe Leu Gln Pro Ala Gln
            500                 505                 510

Ser Ile Asn Tyr Val Glu Cys His Asp Asn His Thr Phe Trp Asp Lys
        515                 520                 525

Met Ala Leu Cys Phe Glu Glu Asp Ala Asp Thr Lys Arg Leu Arg Gln
    530                 535                 540

Arg Leu Ala Val Ser Ile Val Leu Leu Ser Gln Gly Val Pro Phe Leu
545                 550                 555                 560

His Ala Gly Gln Glu Phe Cys Arg Thr Lys Asn Gly Asp Ser Asn Ser
                565                 570                 575

Tyr Arg Ser Gly Asp Asp Ile Asn Lys Leu Asp Trp Glu Lys Arg Ala
            580                 585                 590
```

```
Glu Leu Cys Glu Asp Val Glu Tyr Val Arg Gln Leu Ile Arg Leu Arg
        595             600             605

Arg Ser His Pro Ala Phe Arg Leu Gln Lys Glu Glu Glu Val Lys Glu
    610             615             620

His Leu Ser Phe Met Asp Gly Thr Gly Glu Val Thr Ala Tyr Lys Leu
625             630             635                         640

Lys Asn Ile Ala Ala Ile Asp Pro Trp Asn Glu Ile Ile Val Val His
            645             650             655

Cys Pro Phe Ala Lys Lys Glu Thr Leu Lys Leu Pro Asp Gln Lys Gln
            660             665             670

Tyr Leu Leu His Cys Asp Pro Phe Thr Phe Phe Asn Gly Lys Val Gln
        675             680             685

Ala Glu Lys Arg Leu Arg Leu Asn Gly Ile Gly Thr Tyr Val Leu Tyr
        690             695             700

Glu Pro Lys Gly Ile Phe
705             710
```

METHOD FOR MAKING MUTATED PULLULANASE ENZYME, MUTATED PULLULANASE ENZYME, AND MICROORGANISM EXPRESSING THE SAME

CROSS REFERENCE TO RELATED APPLICATIONS

This application is a continuation-in-part of U.S. application Ser. No. 12/309,929, filed on Jul. 7, 2009, which is a National Stage Entry of PCT/JP2007/062996, filed on Jun. 28, 2007, which claims priority to Japanese application No. 2006-213490, filed on Aug. 4, 2006, all of which are hereby incorporated by reference in their entireties.

INCORPORATION BY REFERENCE

In compliance with 37 C.F.R. § 1.52(e)(5), the Sequence Listing in electronic file name: P06081_PUC1_amano_ST25.txt; size 52.5 KB; created on: Dec. 29, 2015, using Patent-In 3.5, and Checker 4.4.0 is hereby incorporated by reference in its entirety.

FIELD OF THE INVENTION

The present invention relates to a method for designing a mutated enzyme hydrolyzing an α-1,6-glycosidic linkage, a method for preparing the same, and a mutated enzyme.

BACKGROUND OF THE INVENTION

Pullulanase (EC 3.2.1.41) is an enzyme hydrolyzing an α-1,6 linkage of, for example, amylopectin in starch. Pullulanase is an enzyme having a high industrial applicability in the fields of sugar, for example, production of maltooligosaccharides such as glucose, maltose, maltotriose, maltotetraose, maltopentaose and maltohexaose (OLIGOSACCHARIDES, Gordon and Breach Science Publishers, p3), improvement of rice cooking (patent document 1), and the like.

Pullulanase derived from microorganism includes Bacillus sp. APC-9603 (patent document 2), and ones derived from Klebsiella pneumonia (AMANO ENZYME INC.), Bacillus deramificans, Bacillus acidpullulyticus, Bacillus stearothermophilus, Bacillus sectorramus, Bacillus circulans, Bacillus cereus, and Bacillus sectorramus.

Similar to the other enzymes, when pullulanase is used, concentration of substrate and enzyme, reaction temperatures, reaction time, and the like are adjusted depending upon the applications of use. However, with adjustment of such enzyme reaction conditions alone, it may not be possible to produce intended products or to obtain an expected yield. Thus, it has been necessary to modify the properties themselves of pullulanase.

In order to modify the properties of pullulanase, it is necessary that mutants of pullulanase should be produced, and the activity, substrate specificity, and the like, should be evaluated so as to search for an excellent mutant. However, such processes have required much labor. Patent document 3 discloses one example of a mutant of pullulanase.

Patent document 1: JP H7-289186 A
Patent document 2: JP H5-292962 A
Patent document 3: JP 2002-505108 A
Non-patent document 1: J Mol Biol. 2006 Jun. 9; 359 (3): 690-707

SUMMARY OF THE INVENTION

One of objects of the present invention is to provide a novel method for improving an enzyme hydrolyzing an α-1,6-glycosidic linkage. Another object of the present invention is to provide a mutated enzyme whose action properties have been improved. With the change in action property, it is possible to reduce the amount of enzyme to be used, to shorten a reaction time, to increase applications of use, and the like.

In order to solve the above-mentioned problems, the present inventors have keenly investigated further. As a result, the present inventors have obtained an important finding regarding the recognition of a substrate in pullulanase derived from Bacillus subtilis strain 168 by making good use of an X-ray analysis technology for a crystalline structure. That is to say, regarding the pullulanase, the present inventors have succeeded in crystallizing it into a state containing a substrate analog (α-cyclodextrin), and in obtaining information about the three-dimensional structure thereof. Thereby, they have clarified a site to which a substrate analog is bound. Thus, amino acid that is thought to be involved in recognition of a substrate has been specified. Furthermore, as a result of comparison between the three-dimensional structure of the pullulanase and the three-dimensional structure of the same kinds of enzymes derived from the other microorganisms, high similarity is recognized as a whole. In particular, it has been determined that the similarity is extremely high in the site relating to the recognition of a substrate. Since such a high similarity is recognized, it is predicted that an amino acid corresponding to the amino acid specified in the above-mentioned pullulanase plays an important role in the recognition of a substrate in each enzyme.

By the way, as to pullulanase of Klebsiella pneumoniae that is one of the enzymes used in the investigation at this time, an active site is searched for by using G4 (maltotetraose) (see, non-patent document 1). The binding site of the substrate indicated therein is located in the vicinity of the binding site of a substrate analog predicted by the above-mentioned method (a method by comparing with pullulanase derived from Bacillus subtilis strain 168). This fact supports the involvement of the binding site of the substrate analog successfully found by the present inventors in the recognition of actual substrate.

The present invention is mainly based on the above-mentioned results and provides a designing method of an enzyme mentioned below.

[1] A method for making a mutated pullulanase enzyme that hydrolyzes an α-1,6-glycosidic linkage, the method comprising following steps:

(1) obtaining the amino acid sequence of a pullulanase enzyme having an amino acid sequence that is at least 95% identical to the amino acid sequence set forth in SEQ ID NO: 14;

(2) identifying an amino acid to be mutated in the pullulanase enzyme of step (1), wherein said amino acid to be mutated corresponds to the amino acid at position $Phe^{476}$ of SEQ ID NO: 2;

(3) constructing a mutated amino acid sequence by substituting the amino acid to be mutated with another amino acid or deleting the amino acid to be mutated, thereby making a mutated pullulanase enzyme having the mutated amino acid sequence that has increased affinity for pullulan and that hydrolyzes an α-1,6-glycosidic linkage.

[2] A method for making a mutated pullulanase enzyme that hydrolyzes an α-1,6-glycosidic linkage, the method comprising following steps:

(1) obtaining the amino acid sequence of a pullulanase enzyme having an amino acid sequence that is at least 95% identical to the amino acid sequence set forth in any one of SEQ ID NOs: 2, 13 and 17;

(2) identifying an amino acid to be mutated in the pullulanase enzyme of step (1), wherein said amino acid to be mutated corresponds to the amino acid at position Phe$^{476}$ of SEQ ID NO: 2;

(3) constructing a mutated amino acid sequence by substituting the amino acid to be mutated with another amino acid or deleting the amino acid to be mutated, thereby making a mutated pullulanase enzyme having the mutated amino acid sequence that has increased affinity for amylopectin and that hydrolyzes an α-1,6-glycosidic linkage.

[3] The method according to [1], the identification of step (2) is achieved by a sequence alignment comparison or a three-dimensional-structure comparison between SEQ ID NO: 2 and the amino acid sequence of the pullulanase enzyme of step (1).

[4] The method according to [2], the identification of step (2) is achieved by a sequence alignment comparison or a three-dimensional-structure comparison between SEQ ID NO: 2 and the amino acid sequence of the pullulanase enzyme of step (1).

[5] The method according to [1], further comprising a step of substituting or deleting in the mutated amino acid sequence one or more amino acids selected from the group consisting of the amino acid corresponding to position 292, the amino acid corresponding to position 371, the amino acid corresponding to position 406, the amino acid corresponding to position 407, the amino acid corresponding to position 437, the amino acid corresponding to position 465, the amino acid corresponding to position 475, the amino acid corresponding to position 525, the amino acid corresponding to position 526, the amino acid corresponding to position 580, and the amino acid corresponding to position 582 of SEQ ID NO: 2.

[6] The method according to [2], further comprising a step of substituting or deleting in the mutated amino acid sequence one or more amino acids selected from the group consisting of the amino acid corresponding to position 292, the amino acid corresponding to position 371, the amino acid corresponding to position 406, the amino acid corresponding to position 407, the amino acid corresponding to position 437, the amino acid corresponding to position 465, the amino acid corresponding to position 475, the amino acid corresponding to position 525, the amino acid corresponding to position 526, the amino acid corresponding to position 580, and the amino acid corresponding to position 582 of SEQ ID NO: 2.

[7] A mutant enzyme obtained by the method of [1].

[8] A mutant enzyme obtained by the method of [2].

[9] A recombinant nucleic acid encoding the mutant enzyme of [7].

[10] A recombinant nucleic acid encoding the mutant enzyme of [8].

[11] A transgenic microorganism comprising the recombinant nucleic acid of [9].

[12] A transgenic microorganism comprising the recombinant nucleic acid of [10].

BRIEF DESCRIPTION OF THE DRAWINGS

FIG. 6 shows a multiple alignment of amino acid sequences of five kinds of pullulanase and isoamylase. BSP: pullulanase of *Bacillus subtilis*, BCP: pullulanase of *Bacillus* sp. APC-9603, BDP: pullulanase of *Bacillus deramificans*, KPP: pullulanase of *Klebsiella pneumoniae*, PIA: isoamylase of *Pseudomonas amyloderamosa* (Amemura, A., Chakraborty, R., Fujita, M., Noumi, T. and Futai, M., Cloning and nucleotide sequence of the isoamylase gene from *Pseudomonas amyloderamosa* SB-15, JOURNAL J. Biol. Chem. 263 (19), 9271-9275 (1988)). *: position of an amino acid that has been deduced to be involved in binding to α-cyclodextrin, +: amino acid that has been deduced to be involved in binding to G4 altotetraose) among amino acids that have been deduced to be involved in binding to α-cyclodextrin in the above-mentioned report, –: position of the amino acid that has been deduced to be involved in binding to α-cyclodextrin in the above-mentioned report (excluding the position of amino acid that has been deduced to be involved in binding to α-cyclodextrin). Pul/Iso (pullulanase/isoamylase) specific region, region I, region II, region III and region IV are shown by a shaded area. Furthermore, an amino acid of the active site is surrounded by square.

FIG. 8 shows an alignment of the amino acid sequence of pullulanase of *Bacillus subtilis* (BSP) and the amino acid sequence of pullulanase of *Bacillus licheniformis* (BLP).

DETAILED DESCRIPTION OF THE INVENTION

1. Designing Method of Mutated Enzyme

Figure 1:
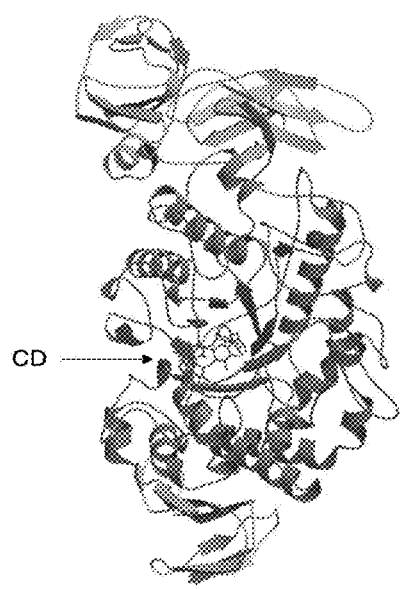
FIG. 1 is a view showing a three-dimensional structure of *Bacillus subtilis* pullulanase having α-cyclodextrin as a ligand, which is shown by the use of a ribbon model. CD: α-cyclodextrin.

A first aspect of the present invention provides a designing method of a mutated enzyme based on an enzyme hydrolyzing an α-1,6-glycosidic linkage. With the designing method of the present invention, it is possible to obtain an enzyme that is different from the enzyme before mutation in terms of action properties. In other words, the designing method of the present invention is used as a technique for changing the action properties of an enzyme. Specifically, for example, the designing method of the present invention can be used for the purpose of improving the activity and/or substrate specificity of pullulanase with respect to pullulan, or the activity and/or substrate specificity of pullulanase with respect to amylopectin. It can be expected that the improvement of the activity enables obtaining of a sufficient effect with less amount. That is to say, reduction of the amount to be used can be expected. On the other hand, the improvement of the substrate specificity facilitates the use thereof and reduces the amount to be used.

Furthermore, if different substrate specificities are provided, a novel application of use can be achieved.

Pullulanase that is one of the enzymes hydrolyzing an α-1,6-glycosidic linkage can act on amylopectin in starch so as to form straight chain amylase. By the use of this characteristic, pullulanase has been widely used for processing starch, production of glucose, maltose, oligosaccharide, or the like, or brewing. Furthermore, pullulanase is an enzyme that is used for various industrial purposes of, for example, manufacturing a material of thermally stable microcapsule, a carrier of an immobilized enzyme, and the like. If the reactivity with respect to α-1,6 binding can be freely changed, for example, it is possible to increase the yield in products, to reduce the amount of enzyme to be used (an amount to be added). At the same time, this enzyme can be applied to new fields.

In the present specification, unless otherwise noted, the term "action property" is used as a term including properties (including activity and substrate specificity with respect to pullulan and activity and substrate specificity with respect to amylopectin) relating to the actions for hydrolyzing an α-1,6-glycosidic linkage. The evaluation of the "action property" can be carried out by using the Km value, Kcat value, and the like, obtained by the test system using pullulan, amylopectin, and starch as a substrate. Km value, Kcat value can be determined by the following method.

(1) Substrates (for example, pullulan or amylopectin) with various concentrations are dissolved in 50 mM acetate buffer (pH 5.6) and reacted at 25° C.
(2) The concentration of a reducing sugar contained in a regularly sampled reaction solution is determined by a Park-Johnson method, and the reaction rate is measured from the increasing rate of the reducing sugar.
(3) Km value and Kcat value are obtained by curve fitting into Michaelis-Menten equation by the non-linear minimum square method.

Note here that although depending upon the experiment conditions, by comparing the concentrations of the reducing sugar contained in the reaction solution at certain points, the action properties of two enzymes can be compared and evaluated.

The designing method of the mutated enzyme of the present invention includes roughly two steps, that is, a step of specifying an amino acid to be mutated (step (1)) and a step of constructing an amino acid sequence of the mutated amino acid (step (2)). Hereinafter, the respective steps are described in detail. Note here that in this specification, an enzyme as a base in designing a mutated enzyme (an enzyme to which mutation is carried out) is referred to as "enzyme to be mutated."

Step (1)

In step (1), in an amino acid sequence of an enzyme (enzyme to be mutated) hydrolyzing an α-1,6-glycosidic linkage, one or two or more of amino acid(s) to which mutation is carried out (hereinafter, which is also referred to as "amino acid to be mutated") is specified. The amino acid to be mutated of the present invention is selected from the group shown below in an amino acid sequence of an enzyme that hydrolyzes an α-1,6-glycosidic linkage, that is, the group consisting of an amino acid corresponding to an amino acid at the 292 position, an amino acid corresponding to an amino acid at the 371 position, an amino acid corresponding to an amino acid at the 406 position, an amino acid corresponding to an amino acid at the 407 position, an amino acid corresponding to an amino acid at the 437 position, an amino acid corresponding to an amino acid at the 465 position, an amino acid corresponding to an amino acid at the 475 position, an amino acid corresponding to an amino acid at the 476 position; an amino acid corresponding to an amino acid at the 525 position, an amino acid corresponding to an amino acid at the 526 position, an amino acid corresponding to an amino acid at the 580 position and an amino acid corresponding to an amino acid at the 582 position of the amino acid sequence set forth in SEQ ID NO: 2. Note here that these amino acids to be mutated are amino acids that have been suggested to be involved in the recognition of the substrate as a result of analysis of the three-dimensional structure at the time of binding of a substrate analog (α-cyclodextrin, hereinafter, referred to as "CD") regarding pullulanase derived from *Bacillus subtilis* strain 168 (including the amino acid sequence set force in SEQ ID NO: 2), and from the comparison results between this three-dimensional structure and the three-dimensional structure of an enzyme derived from a microorganism. By mutating these amino acids, it is expected that the action property (in particular, substrate specificity) of the enzyme is changed.

Herein, the term "corresponding" to be used for amino acid residues in the specification means the equal contribution to exhibition of the function between proteins (enzymes) to be compared. In particular, it means that the contribution to the substrate specificity is equivalent. For example, when an amino acid sequence to be compared is arranged with respect to the reference amino acid sequence (that is to say, amino acid sequence set forth in SEQ ID NO: 2) so that suitable comparison can be carried out while considering the partial homology of the primary structure (that is to say, an amino acid sequence) (at this time, a gap may be introduced so as to optimize the alignment if necessary), an amino acid in a position corresponding to a certain amino acid in the reference to amino acid sequence can be defined as "corresponding amino acid." Instead of comparison between primary structures, or in addition thereto, by comparison between the stereostructures (three-dimensional structures), "corresponding amino acid" can be specified. By using the three-dimensional structure information, it is possible to comparison results with high reliability. In this case, atomic coordinates of the three-dimensional structures of a plurality of enzymes can be compared with each other so as to carry out alignment. The three-dimensional structure information on the enzyme to be mutated can be obtained from, for example, Protein Data Bank.

An example of the method of determining the three-dimensional structure of protein by an X-ray analysis of crystalline structure is described below.

(1) Protein is crystallized. The crystallization is indispensable for determination of the three-dimensional structure. Besides, the crystallization is industrially useful as a purification of protein with high purity and a preservation method of protein with high density. In this case, protein to which a substrate or an analog compound thereof is bound as a ligand may be crystallized.

(2) The prepared crystal is irradiated with X ray and analysis data are collected. Note here that protein crystal may be damaged by X ray irradiation and may be deteriorated in its diffraction ability so often. In such a case, a low-temperature measurement method for rapidly cooling a crystal to about −173° C. and collecting diffraction data in this state has been recently widespread. Note here that finally, in order to collect high resolution data used for determining a structure, synchrotron radiation light with high intensity is used.

(3) For carrying out analysis of a crystalline structure, phase information is necessary in addition to the diffraction data. When the crystalline structure of a related protein with respect to the intended protein is not known, it is impossible to determine the structure by a molecule substitution method. Problem as to the phase must be resolved by the heavy atom isomorphous replacement method. The heavy atom isomorphous replacement method is a method of introducing a metal atom having a larger atomic number such as mercury and platinum into a crystal and using the contribution of the metal atom to X-ray diffraction data of X-ray scattering power, thereby obtaining phase information. The determined phase can be improved by smoothing the electron density in the solvent region in the crystal. Since the water molecule in the solvent region is largely fluctuated, electrical density is hardly observed. Therefore, by approximating the electron density in this region to 0, it can approach to the real electron density. Consequently, the phase is improved. Furthermore, when a plurality of molecules are included in an asymmetrical unit, by averaging the electron densities of these molecules, the phase is further radically improved. A protein model is fitted to the view of the electron density calculated by using the thus improved phase. This process is carried out by using a program such as QUANTA (MSI, America) on a computer graphics. Thereafter, by using a program such as X-PLOR (MSI), refinement of the structure is carried out. Thus, the structure analysis is completed.

When the crystalline structure of a related protein with respect to the intended protein is known, the structure can be determined by a molecule substitution method by using an atomic coordinate of the known protein. The molecule substitution and structure refinement can be carried out by using a program such as CNS_SOLVE ver.11.

The present inventors have tried to crystallize the recombinant pullulanase purified from *Bacillus subtilis* strain 168 and to crystallize the pullulanase in a state in which it contains CD as a substrate analog and have succeeded in obtaining three-dimensional structure of both types of pullulanase. Note here that atomic coordinates of the three-dimensional structure of the pullulanase containing CD are shown in the last part of this specification. Furthermore, the amino acid sequence of pullulanase and the base sequence of a gene encoding thereof are shown in SEQ ID NO: 2 and SEQ ID NO: 1 in the sequence listing, respectively.

Figure 2:
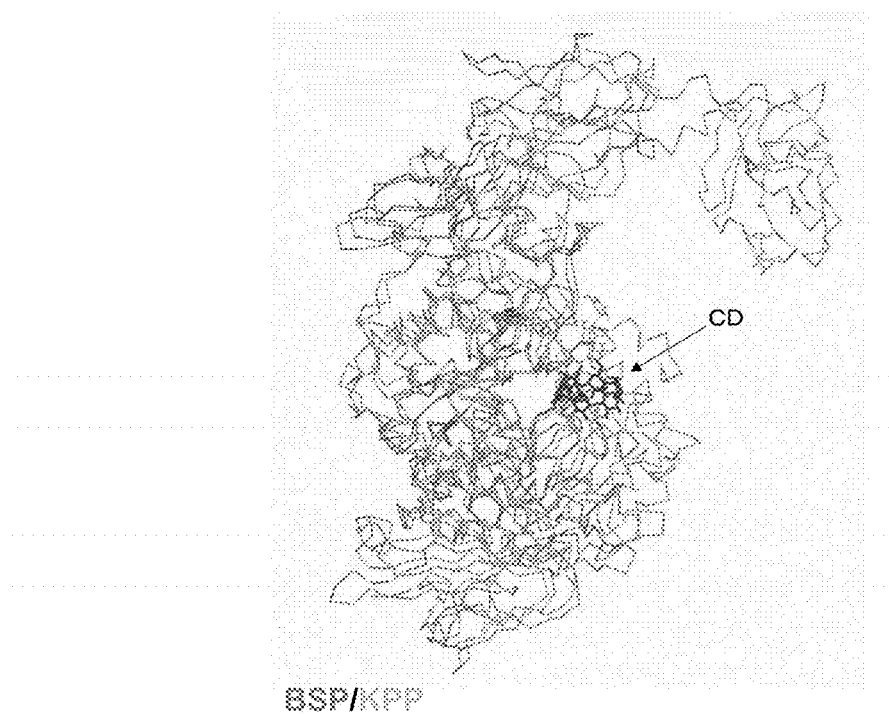
FIG. 2 is a view shown by superimposing *Bacillus subtilis* pullulanase (BSP) having α-cyclodextrin as a ligand and a carbon of pullulanase (KPP) *Klebsiella* pneumonia onto each other. CD: α-cyclodextrin.
Figure 3:
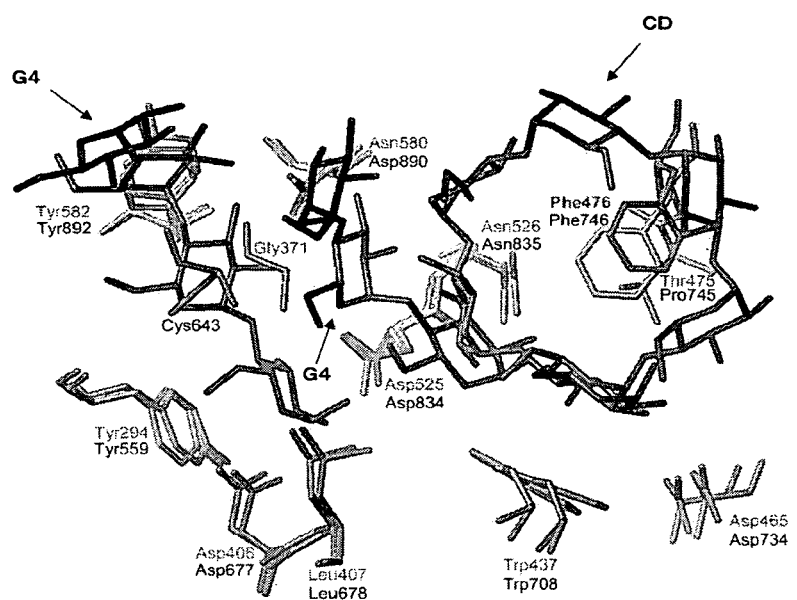
FIG. 3 is an enlarged view showing a substrate binding region of FIG. 2. CD: α-cyclodextrin, G4: maltotetraose. An amino acid of *Bacillus subtilis* pullulanase (upper stage) and an amino acid of pullulanase of *Klebsiella* pneumonia (lower stage) corresponding to the amino acid of the upper stage are shown.

As shown in the below-mentioned Examples, it has been determined that the pullulanase molecule derived from *Bacillus subtilis* strain 168 has rhombic system P2(1)2(1)2 (1) having 70.568×127.68×189.25 Å (see, FIGS. 1 to 3). FIG. 1 is a view showing a crystalline structure of pullulanase by a ribbon model. α-helix and β-sheet are shown in a helix shape and an arrow shape, respectively (FIG. 1), and a substrate analog (CD) is shown by an arrow CD (FIGS. 1 to 3). FIG. 2 is a view shown by superimposing *Bacillus subtilis* pullulanase (BSP) having α-cyclodextrin as a ligand and a carbon of pullulanase (KPP) *Klebsiella* pneumonia onto each other. FIG. 3 is an enlarged view of a substrate binding region of FIG. 2.

In one preferable embodiment of the present invention, the amino acid to be mutated is selected from the group consisting of an amino acid corresponding to an amino acid at the 292 position, an amino acid corresponding to an amino acid at the 371 position, an amino acid corresponding to an amino acid at the 407 position, an amino acid corresponding to an amino acid at the 475 position, an amino acid corresponding to an amino acid at the 476 position and an amino acid corresponding to an amino acid at the 582 position of the amino acid sequence set forth in SEQ ID NO: 2. Note here that amino acids to be mutated are an amino acid corresponding to an amino acid that has been determined to be directly involved in binding between pullulanase derived from *Bacillus subtilis* strain 168 and a substrate analog (CD).

By the way, it has clarified that an amino acid at the 476 position of the amino acid sequence set forth in SEQ ID NO: 2 is arranged so that it enters a ring structure of CD that is a substrate analog in the three-dimensional structure analysis about pullulanase derived from *Bacillus subtilis* strain 168, and this amino acid is thought to play an important role in the recognition of a substrate. Therefore, in the further preferable embodiment of the present invention, an amino acid corresponding to the amino acid is to be an amino acid to be mutated.

The kinds, origins and the like of enzymes to be mutated in accordance with the present invention are not particularly limited as long as the enzymes hydrolyze an α-1,6-glycosidic linkage. Preferably, the enzyme to be mutated is pullulanase or isoamylase derived from microorganisms. An example of the microorganism herein can include a microorganism of genus *bacillus*, a microorganism of genus *Klebsiella*, or a microorganism of genus *pseudomonas*. As the pullulanase derived from microorganism, *Bacillus* sp. APC-9603 (Japanese Patent Unexamined Publication No. H5-292962), and ones derived from derived from *Klebsiella* pneumonia (AMANO ENZYME INC.), *Bacillus deramificans*, *Bacillus acidpullulyticus*, *Bacillus stearothermophilus*, *Bacillus sectorramus*, *Bacillus circulans*, *Bacillus cereus*, and *Bacillus subtilis* strain 168 are well known. For example, any of them can be employed as the enzyme to be mutated in the present invention. Furthermore, isoamylase of *Pseudomonas amyloderamosa* can be employed as the enzyme to be mutated in the present invention. A specific example of the enzyme to be mutated includes an enzyme (pullulanase of *Bacillus subtilis* strain 168) consisting of an amino acid sequence set forth in SEQ ID NO: 2, an enzyme (pullulanase of *Klebsiella pneumoniae* ATCC9621) consisting of an amino acid sequence set forth in SEQ ID NO: 13, an enzyme (pullulanase of *Bacillus* sp. APC-9603) consisting of an amino acid sequence set forth in SEQ ID NO: 14, an enzyme (pullulanase of *Bacillus deramificans*) consisting of an amino acid sequence set forth in SEQ ID NO: 15, an enzyme (isoamylase of *Pseudomonas amyloderamosa*) consisting of an amino acid sequence set forth in SEQ ID NO: 16, and an enzyme (pullulanase of *Bacillus licheniformis*) consisting of an amino acid sequence set forth in SEQ ID NO: 17.

It is preferable that an enzyme consisting of an amino acid sequence having a high identity with the amino acid sequence set forth in SEQ ID NO: 2 is an enzyme to be mutated. It is preferable because effective improvement is expected to be achieved and the specification of the amino acid to be mutated is facilitated.

Specifically, it is preferable that the enzyme to be mutated is an enzyme consisting of an amino acid sequence having 70% or more identity with the amino acid sequence set forth in SEQ ID NO: 2. Herein, the higher identity is generally more preferable. For example, the enzyme to be mutated is an enzyme consisting of an amino acid sequence having the identity of preferably 80% or more, further preferably 90% or more, and further preferably 95% or more.

Herein, the identity (%) between two amino acid sequences can be determined by the following procedure. Firstly, two sequences are aligned for optimum comparison of the two sequences (for example, a gap may be introduced in the first sequence so as to obtain an optimum alignment with the second sequence). When a molecule (amino acid residue) at the specific position in the first sequence and a molecule in the corresponding position in the second sequence are the same, the molecules in the positions are defined as being identical. The identity between two sequences is an action property of the number of identical positions shared by the sequences (i.e., identity (%)=number of identical positions/total number of positions×100), preferably taking into account the number of gaps, and the length of each gap, which need to be introduced for optimal alignment of the two sequences.

The comparison and determination of identity between two sequences can be carried out by using a mathematical algorithm. A specific example of mathematical algorithm that can be used for comparing sequences include an algorithm described in Karlin and Altschul (1990) Proc. Natl. Acad. Sci. USA 87:2264-68 and modified by Karlin and Altschul (1993) Proc. Natl. Acad. Sci. USA 90:5873-77 but the algorithm is not limited to this. Such an algorithm is incorporated in NBLAST and XBLAST programs (version 2.0) of Altschul et al. (1990) J. Mol. Biol. 215: 403-10. BLAST polypeptide searches may be carried out by, for example, the NBLAST program, score=50, wordlength=3 to obtain amino acid sequence homologous to a certain amino acid sequence. To obtain gapped alignments for comparison purposes, Gapped BLAST as described in Altschul et al., (1997) Amino Acids Research 25(17): 3389-3402 can be utilized. When utilizing BLAST and Gapped BLAST programs, the default parameters of the respective programs (e.g., XBLAST and NBLAST) can be used. Another example of mathematical algorithm that can be used for comparing sequences includes an algorithm of Meyers and Miller (Comput. Appl. Biosci. 4: 11-17 (1988)) which has been incorporated into the ALIGN program that can be used for, for example, GENESTREAM network server (IGH Montpellier, France) or ISREC server. When the ALIGN program is used for comparison of the amino acid sequences, for example, a PAM120 weight residue table can be used with a gap length penalty of 12 and a gap penalty of 4.

The identity between two amino acid sequences can be determined using the GAP program in the GCG software package, using a Blossom 62 matrix or PAM250 matrix and a gap weight of 12, 10, 8, 6, or 4, and a gap length weight of 2, 3, or 4.

Furthermore, the homology between two nucleic acid sequences can be determined using the GAP program in the GCG software package with a gap weight of 50 and a gap length weight of 3.

The enzyme to be mutated is typically a wild type enzyme (naturally occurring enzyme). However, an enzyme to which some mutation or modification has already been given is not excluded. Thus, the present invention can be used for the purpose of further improving the property of an enzyme.

Step (2)

In the step (2), an amino acid sequence, in which an amino acid specified in the step (1) has been substituted with another amino acid or the amino acid has been deleted, is constructed based on an amino acid sequence of the enzyme to be mutated. The kinds of substituted amino acids are not particularly limited and therefore may include conservative substitution of amino acid or non-conservative substitution of amino acid. Herein, a "conservative amino acid substitution" is one in which the amino acid residue is substituted with an amino acid residue having a side chain with similar feature. The amino acid residues are divided into some families including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). Preferably, the conservative amino acid substitution is a substitution between preferably an amino acid residue of the same family.

2. Preparation Method of Mutated Enzyme

A second aspect of the present invention relates to a preparation method of a mutated enzyme. The preparation method in accordance with the present invention includes the following steps:

(1) preparing nucleic acid encoding an amino acid sequence constructed by the designing method in accordance with the present invention;

(2) expressing the nucleic acid; and (3) collecting expression products.

In the step (1), necessary mutation (that is, substitution or deletion of amino acids in a certain position in protein as an expression product) is applied to a gene encoding the enzyme to be mutated based on an amino acid sequence constructed by the designing method of the present invention, and thereby nucleic acid (gene) encoding a mutated enzyme is obtained. A large number of methods for the position specific substitution of base sequence have been known (see, for example, Molecular Cloning, Third Edition, Cold Spring Harbor Laboratory Press, New York). Among them, appropriate methods can be selected and used.

As the position specific mutation introduction method, a position specific amino acid saturated mutation method can be employed. The position specific amino acid saturated mutation method is a "Semi-rational, semi-random" technique in which a position relating to the intended function is deduced based on the three-dimensional structure of protein, and the amino acid saturated mutation is introduced (J. Mol. Biol. 331, 585-592 (2003)). For example, a position specific amino acid saturated mutation can be introduced by using a kit such as Quick change (Stratagene), Overlap extension PCR (Nucleic Acid Res. 16, 7351-7367 (1988)). As DNA polymerase used for PCR, Taq polymerase can be used. However, it is preferable that DNA polymerase with high purify, for example, KOD-PLUS-(TOYOBO), Pfu turbo (Stratagene) are used.

On the other hand, a gene encoding a mutated enzyme can be prepared by inserting random mutation into an enzyme gene, comparing the substrate specificities of expression product by mutants each other, and selecting a gene having preferable substrate specificity. When such a random mutation is introduced, firstly, for example, error-prone PCR is used and mutation is introduced into a targeted gene region randomly so as to construct a mutated enzyme gene library. Then, a clone is selected from the resultant library using the enzymatic activity or the substrate specificity as an index.

In the step (2), a gene prepared in the step (1) is expressed. Then, in the subsequent step (3), mutated enzymes as expression products are collected.

In general, from the step of expressing a gene to the step of collecting the expression products (mutated enzymes) are carried out by using an appropriate host-vector system. However, a cell-free synthesis system may be used. As to the detail of the preparation method of the mutated enzyme by using a host-vector system, the below-mentioned description may be employed (see, the column of 4. Nucleic acid encoding mutated enzyme).

Herein, the "cell-free synthesis system (cell-free transcription system, cell-free transcription/translation system)" denotes that living cells are not used but a ribosome derived from living cells (or cells obtained by genetically engineering technique) or by using a transcription/translation factor and the like, mRNA or protein encoded by nucleic acid (DNA or mRNA) as a template are synthesized from them in vitro. In general, in the cell-free synthesis system, a cell extract obtained by purifying a cell homogenized solution if necessary is used. In general, a cell extract includes ribosome necessary to synthesis of protein, various factors such an initiation factor, various enzymes such as tRNA. When synthesis of protein is carried out, various amino acids, energy sources such as ATP and GTP, creatine phosphate, and the like, are added to the cell extract solution. Needless to say, at the time of synthesis of protein, additionally prepared ribosome or various factors, and/or various enzymes may be replenished if necessary.

Development of a transcription/translation system in which each molecule (factor) necessary to synthesis of protein is reconstructed has been reported (Shimizu, Y. et al.: Nature Biotech., 19, 751-755, 2001). In this system, a gene of 31 kinds of factors consisting of three kinds of initiation factors constituting a protein synthesis system of bacteria, three kinds of elongation factors, four kinds of factors involved in termination, 20 kinds of aminoacyl tRNA synthases for binding each amino acid to tRNA, and methionyl tRNA formyl transferase is amplified from *Escherichia coli* genome. They are used so as to reconstruct a protein synthesis system in vitro. In the present invention, such a re-constructed synthesis system may be used.

The term "cell-free transcription/translation system" can be used interchangeably with the term cell-free protein synthesis system, in vitro translation system or in vitro transcription/translation system. In the in vitro translation system, protein is synthesized by using RNA as a template. As the template RNA, total RNA, mRNA, in vitro transcription product, and the like, are used. On the other hand, in the in vitro transcription/translation system, DNA is used as a template. The template DNA should include a ribosome-binding region and preferably includes an appropriate terminator sequence. Note here that the in vitro transcription/translation system sets a condition in which factors necessary to reaction are added so that the transcription reaction and translation reaction proceed consecutively.

3. Mutated Enzyme

According to the above-mentioned preparation method, it is possible to obtain a mutated enzyme in which the action property with respect to α-1,6-glycosidic linkage has been changed. Then, a further aspect of the present invention provides a mutated enzyme. In the mutated enzyme of the present invention, an action property with respect to pullulan or action property with respect to amylopectin are improved over the enzyme to be mutated.

The mutated enzyme of the present invention is an amino acid sequence wherein in the amino acid sequence of enzyme (enzyme to be mutated) hydrolyzing an α-1,6-glycosidic linkage, one or two or more amino acids selected from the group consisting of an amino acid corresponding to an amino acid at the 292 position, an amino acid corresponding to an amino acid at the 371 position, an amino acid corresponding to an amino acid at the 406 position, an amino acid corresponding to an amino acid at the 407 position, an amino acid corresponding to an amino acid at the 437 position, an amino acid corresponding to an amino acid at the 465 position, an amino acid corresponding to an amino acid at the 475 position, an amino acid corresponding to an amino acid at the 476 position; an amino acid corresponding to an amino acid at the 525 position, an amino acid corresponding to an amino acid at the 526 position, an amino acid corresponding to an amino acid at the 580 position and an amino acid corresponding to an amino acid at the 582 position of the amino acid sequence set forth in SEQ ID NO: 2 is/are substituted with another amino acid or deleted.

Preferably, the substituted or deleted amino acid is one or two or more amino acid selected from the group consisting of an amino acid corresponding to an amino acid at the 292 position, an amino acid corresponding to an amino acid at the 371 position, an amino acid corresponding to an amino acid at the 407 position, an amino acid corresponding to an amino acid at the 475 position, an amino acid corresponding to an amino acid at the 476 position, and an amino acid corresponding to an amino acid at the 582 position of the amino acid sequence set forth in SEQ ID NO: 2.

Further preferably, the substituted or deleted amino acid is an amino acid corresponding to an amino acid at the 476 position of the amino acid sequence set forth in SEQ ID NO: 2.

The kinds, origins and the like of the enzymes to be mutated are the same as those in the above-mentioned first aspect, and therefore the same description is omitted herein. A specific example of the enzyme to be mutated includes an enzyme (pullulanase of *Bacillus subtilis* strain 168) consisting of an amino acid sequence set forth in SEQ ID NO:2, an enzyme (pullulanase of *Klebsiella pneumoniae* ATCC9621) consisting of an amino acid sequence set forth in SEQ ID NO: 13, an enzyme (pullulanase of *Bacillus* sp. APC-9603) consisting of an amino acid sequence set forth in SEQ ID NO: 14, an enzyme (pullulanase of *Bacillus deramificans*) consisting of an amino acid sequence set forth in SEQ ID NO: 15, an enzyme (isoamylase of Pseudomonas amyloderamosa) consisting of an amino acid sequence set forth in SEQ ID NO:16 and an enzyme (pullulanase of *Bacillus licheniformis*) consisting of an amino acid sequence set forth in SEQ ID NO: 17.

The mutated enzyme of the present invention is characterized by having an amino acid sequence in which a certain position of the amino acid sequence of the enzyme before mutation (enzyme to be mutated) has been mutated. In a position other than the position related to the mutation, a part of the amino acid may be mutated or modified. Thus, the present invention also provides protein having the same function as compared with the mutated enzyme having the amino acid sequence to which the above-mentioned mutation has been given but having a difference in a part of the amino acid sequence (hereinafter, also referred to as "homologous protein"). The term "having a difference in a part of the amino acid sequence" typically means that the amino acid sequence is mutated (changed) by the deletion and substitution of one to several amino acids constituting the amino acid sequence, or addition of one to several amino acids, or the combination thereof. The difference in the amino acid sequence herein is acceptable as long as the properties related to hydrolysis of an α-1,6-glycosidic linkage are not radically reduced (preferably, in the limit substantially held). As long as this condition is satisfied, the position of difference in the amino acid sequence is not particularly limited and the difference may occur in a plurality of positions. The plurality herein signifies a numerical value corresponding to less than about 30%, preferably less than about 20%, further preferably less than about 10%, yet further preferably less than about 5%, and most preferably less than about 1% with respect to the entire amino acid. That is to say, homologous protein has, for example, about 70% or more, preferably about 80% or more, further preferably about 90% or more, yet further preferably about 95% or more and most preferably about 99% or more of similarly to the amino acid sequence of the mutated enzyme.

The mutated enzyme can be used for arbitrary applications that need hydrolyzing an α-1,6-glycosidic linkage. For example, the mutated enzyme can be used for production of maltooligosaccharide such as glucose, maltose, maltotriose, maltotetraose, maltopentaose, and maltohexaose, and for the improvement of rice cooking, and the like. The amount of the mutated enzyme to be used can be appropriately set so that the intended effect can be exhibited. For example, the enzyme reaction can be carried out under conditions so that the enzyme concentration in the reaction solution becomes about 10 nM to about 100 μM.

4. Nucleic Acid Encoding Mutated Enzyme

The present invention further provides a nucleic acid related to a mutated enzyme of the present invention. That is to say, the present invention provides a gene encoding a mutated enzyme, nucleic acid that can be used as a probe for identifying a nucleic acid encoding a mutated enzyme, and nucleic acid that can be used as a primer for amplifying or mutating a nucleic acid encoding the mutated enzyme.

A gene encoding a mutated enzyme is typically used for preparing a mutated enzyme. A genetically engineering preparation method using a gene encoding a mutated enzyme makes it possible to obtain a mutated enzyme in a more homogeneous state. Furthermore, the method is a suitable for preparing a large amount of mutated enzymes. Note here that the application of the gene encoding a mutated enzyme is not limited to preparation of a mutated enzyme. For example, the nucleic acid can be used as an research tool for the purpose of elucidating the mechanism of action of a mutated enzyme, or as a tool for designing or preparing a further mutant of an enzyme.

In the present invention, the "gene encoding a mutated enzyme" refers to nucleic acid capable of obtaining the mutated enzyme when it is expressed, and includes not only a nucleic acid having a base sequence corresponding to an amino acid sequence of the mutated enzyme but also a nucleic acid obtained by adding a sequence that does not encode the amino acid sequence to the nucleic acid. Furthermore, degeneracy of codon is also considered.

The nucleic acid of the present invention can be prepared in an isolated state by standard genetic engineering technique, molecular biological technique, biochemical technique, and the like, with reference to sequence information disclosed in this specification or attached sequence list.

Another embodiment of the present invention provides nucleic acid that has a base sequence having the same function as the base sequences of a gene encoding a mutated enzyme of the present invention but having a difference in a part of the base sequence (hereinafter, which is also referred to as "homologous nucleic acid." Furthermore, a base sequence specifying the homologous nucleic acid is also referred to as a "homologous base sequence"). An example of the homologous nucleic acid can include DNA encoding a protein including a base sequence in which one or a plurality of bases are substituted, deleted, inserted, added or inverted relative to the base sequences of a gene encoding a mutated enzyme of the present invention and having an activity capable of hydrolyzing an α-1,6-glycosidic linkage. Such substitution, deletion, or the like, may be occurred in a plurality of sites. The "plurality" herein differs depending upon the position or kinds of amino acid residues in a three-dimensional structure of a protein encoded by the nucleic acid codes, but the "plurality" of bases includes, for example, 2 to 40 bases, preferably 2 to 20 bases and more preferably 2 to 10 bases.

The above-mentioned homologous nucleic acid can be obtained by introduction of mutation by, for example, a treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, N.Y.); random mutagenesis (Molecular Cloning, Third Edition, Chapter 13, Cold Spring Harbor Laboratory Press, N.Y.), and the like. Furthermore, homologous nucleic acid can be obtained by other methods such as irradiation with ultraviolet ray.

A further embodiment of the present invention relates to nucleic acid having a base sequence complementary to the base sequence of the gene encoding a mutated enzyme of the present invention. A further embodiment of the present invention provides nucleic acid having a base sequence at least 60%, 70%, 80%, 90%, 95%, 99% or 99.9% identical to the base sequences of the gene encoding a mutated enzyme of the present invention.

A further embodiment of the present invention relates to nucleic acid having a base sequence that hybridizes, under stringent conditions, to the base sequence complementary to the base sequences of the gene encoding a mutated enzyme of the present invention or the homologous base sequence thereof. The "stringent conditions" herein denote a condition in which a so-called specific hybrid is formed and a non-specific hybrid is not formed. Such stringent conditions are well known to the person skilled in the art and can be set with reference to Molecular Cloning (Third Edition, Cold Spring Harbor Laboratory Press, N.Y.) or Current protocols in molecular biology (edited by Frederick M. Ausubel et al., 1987). An example of the stringent conditions includes a condition in which a DNA is incubated in a hybridization solution (50% formamide, 10×SSC (0.15 M NaCl, 15 mM sodium citrate, pH 7.0), 5×Denhardt solution, 1% SDS, 10% dextran sulfate, 10 μg/ml denatured salmon sperm DNA, 50 mM phosphate buffer (pH7.5)) at about 42° C. to about 50° C., followed by washing with 0.1×SSC and 0.1% SDS at about 65° C. to about 70° C. A more preferable example of the stringent conditions can include a condition using a hybridization solution (50% formamide, 5×SSC (0.15 M NaCl, 15 mM sodium citrate, pH 7.0), 1×Denhardt solution, 1% SDS, 10% dextran sulfate, 10 μ/ml denatured salmon sperm DNA, 50 mM phosphate buffer (pH 7.5)).

A further embodiment of the present invention provides a base sequence of the gene encoding a mutated enzyme of the present invention or a nucleic acid (a nucleic acid fragment) having a part of a base sequence complementary to the base sequence. Such a nucleic acid fragment can be used for detecting, identifying and/or amplifying the nucleic acid having a base sequence of a gene encoding a mutated enzyme of the present invention. The nucleic acid fragment is designed to include at least a part for hybridizing a continuous nucleotide part (for example, about 10 to about 100 base length, preferably about 20 to about 100 base length, and further preferably about 30 to about 100 base length) in the base sequence of the gene encoding a mutated enzyme of the present invention.

When the nucleic acid fragment is used as a probe, it can be labeled. Labeling can be carried out by using a fluorescence material, enzyme, and radioactive isotope.

A yet further aspect of the present invention relates to recombinant DNA including a gene of the present invention (a gene encoding a mutated enzyme). The recombinant DNA is provided in a form of, for example, a vector. The term "vector" in this specification refers to a nucleic acid molecule that can transport a nucleic acid inserted therein to the inside of a target such as a cell.

In accordance with the purpose of use (cloning, protein expression), and by considering the kinds of host cells, an appropriate vector is selected. Specific examples of a vector include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec1, pMFa, pYES2, etc.), a vector using insect cells as a host (pAc, pVL, etc.), a vector using mammalian cells as a host (pCDM8, pMT2PC, etc.).

The vector of the present invention is preferably an expression vector. The term "expression vector" is a vector capable of introducing the nucleic acid inserted therein into the target cells (host cells) and expressing in the cells. The expression vector usually includes a promoter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the nucleic acid of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, N.Y., a well-known method using restriction enzyme and DNA ligase).

As the host cell, from the viewpoint of ease in handling, it is preferable that a bacterial cell such as *Escherichia coli* is used. However, the host cell is not limited to the bacterial cell as long as it can reproduce the recombinant DNA and express a gene of the mutated enzyme. As a preferable example of the host includes T7 system promoter, *Escherichia coli* BL21 (DE3) pLysS can be used. In other case, *Escherichia coli* JM109 can be used.

A further aspect of the present invention relates to a microorganism (that is, transformant) carrying a recombinant DNA of the present invention. The microorganism of the present invention can be obtained by the transfection or transformation using the above-mentioned vector of the present invention. For example, a calcium chloride method (J. Mol. Biol., Vol. 53, page 159 (1970)), a Hanahan method (J. Mol. Biol., Vol. 166, page 557 (1983)), a SEM method (Gene, Vol. 96, page 23 (1990)], a method by Chung et al. (Proceeding of the national Academy of Sciences of the USA, Vol. 86, page 2172 (1989)), a calcium phosphate coprecipitation method, electroporation (Potter, H. et al., Proc. Natl. Acad. Sci. U.S.A. 81, 7161-7165 (1984)), lipofection (Feigner, P. L. et al., Proc. Natl. Acad. Sci. U.S.A. 84,7413-7417 (1984)), and the like.

A microorganism of the present invention can be used for producing a mutated enzyme of the present invention. That is to say, a further aspect of the present invention provides a method for producing a mutated enzyme of the present invention by using the above-mentioned microorganism. The production method of the present invention includes at least a step of culturing the above-mentioned microorganism under the conditions in which the mutated enzyme of the present invention is produced. In general, in addition to this step, a step of collecting (separating and purifying) the produced protein is carried out.

The microorganism (transformant) in accordance with the present invention is cultured in a usual manner. As a carbon source to be used for a medium, a carbon compound that can be assimilated may be used. An example may include glucose, sucrose, lactose, maltose, syrup, pyruvic acid, and the like. Furthermore, as a nitrogen source, any available nitrogen compounds may be used. An example may include peptone, meat extract, yeast extract, casein hydrolysate, soybean cake alkali extract, and the like. Besides, salts of phosphate, carbonate, sulfate, magnesium, calcium, potassium, iron, manganese, zinc, and the like, certain amino acids, certain vitamins, can be used if necessary.

On the other hand, the culture temperature can be set 30 to 40° C. (preferably about 37° C.). Culture time can be set considering the growing property of transformant to be cultured or production property of mutated enzyme, and the like. The pH of the medium is adjusted in a range in which the transformant is grown and an enzyme is produced. Preferably, pH of the medium is adjusted to about 6.0 to 9.0 (preferably, around pH 7.0).

A culture solution containing a bacterial body producing a mutated enzyme can be used as an enzyme solution as it is or after concentration or removing of impurities are carried out. Generally, however, a mutated enzyme is once collected from a culture solution or a bacterial body. When the produced mutated enzyme is secreting type protein, the mutated enzyme can be collected from the culture solution, and in other case, the mutated enzyme can be collected from the bacterial body. When the mutated enzyme is collected from the culture solution, purified products of the mutated enzyme can be obtained by, for example, subjecting the culture supernatant to filtering or centrifugation so as to remove insoluble matters, followed by carrying out separation and purification by the combination of vacuum concentration, membrane concentration, salting out using ammonium sulfate and sodium sulfate, fractional precipitation by methanol, ethanol or acetone, dialysis, heat treatment, isoelectric point treatment, various chromatography such as gel filtration chromatography, adsorption chromatography, ion exchange chromatography and affinity chromatography (for example, gel filtration by Sephadex gel (Pharmacia Biotech) and the like, DEAE sepharose CL-6B (Pharmacia Biotech), octyl sepharose CL-6B (Pharmacia Biotech), CM sepharose CL-6B (Pharmacia Biotech)), and the like. On the other hand, when the mutated enzyme is collected from a bacterial body, purified products of the mutated enzyme can be obtained by subjecting a culture solution to filtration and centrifugation to collect a bacterial body, followed by destructing the bacterial body by mechanical method such as pressure treatment and ultrasonication, or by an enzymatic method using lysozyme, and then carrying out separation and purification as mentioned above.

Purified enzyme obtained as mentioned above can be provided in a state of powder by, for example, freeze drying, vacuum drying or spray drying. At this time, a purified enzyme may be solved in phosphate buffer, triethanolamine buffer, Tris hydrochloric acid buffer, GOOD buffer in advance. Preferably, phosphate buffer and triethanolamine buffer can be used. An example of the GOOD buffer may include PIPES, MES or MOPS.

Hereinafter, the present invention is described further specifically. However, the present invention is not limited to these Examples.

EXAMPLES

1. Preparation of *Bacillus Subtilis* Recombinant Pullulanase (1) Cloning of *Bacillus Subtilis* Pullulanase Gene A gene AmyX (GenBank Accesion No. NC 000964) encoding pullulanase, which is found in the genome sequence of *Bacillus subtilus*, was amplified by PCR as follows. A chromosome DNA of *Bacillus subtilis* strain 168 isolated by the method by Sambrook et al. (Molecular Cloning: a laboratory manual, 2nd Edition, Cold Spring harbor Laboratory Press, 1989) was used as a template of PCR, and oligonucleotides of SEQ ID NO: 3 and SEQ ID NO: 4 were synthesized to form a primer. In the PCR reaction, 30 cycles of reactions of 94° C./2 minutes, 94° C./15 seconds—60° C./30 seconds and amplification of 68° C./4 minutes were carried out by using KOD plus system (TOYOBO). The obtained PCR fragment was treated with restriction enzymes NcoI and XhoI, and then linked to plasmid pET21d (Novagen), which had been cleaved with the both restriction enzymes. Thus, an expression plasmid pEBSP was obtained. It was confirmed by determining the base sequence that the obtained PCR fragment encoded pullulanase correctly.

```
                                          SEQ ID NO: 3
5'-GGCCATGGTCAGCATCCGCCGCAGCTTCGA-3'

(underlined part represents a restriction enzyme
NcoI recognition site)

SEQ ID NO: 4
5'-GGCTCGAGTCAAGCAAAACTCTTAAGATCT-3'

(underlined part represents a restriction enzyme
XhoI recognition site)
```

(2) Expression of *Bacillus Subtilis* Recombinant Pullulanase

The above-mentioned expression plasmid was introduced into *Escherichia coli* HMS174 (DE3) (Novagen) by transformation. The obtained transformant was inoculated on LB medium (500 ml) containing 100 μl ampicillin and the medium was shaken at 37° C. At the time when the turbidity at 600 nm reached 0.6 to 0.8, isopropylthiogalactoside (IPTG) was added so that the final concentration became 0.5 mM and further cultured at 18° C. for 60 hours. The bacterial bodies were collected from the culture solution by centrifugation and suspended in a buffer solution (20 mM tris-hydrochloric acid (pH 8.1)/5 mM EDTA/20 mM β-mercaptoethanol/0.2 mM PMSF).

(3) Purification of *Bacillus subtilis* Recombinant Pullulanase

The suspension obtained in (2) was subjected to ultrasonication (4° C., 30 minutes, 200 μA) and then subjected to centrifugation (14000 rpm, 4° C., 30 minutes) to obtain a crude solution. To this solution, 30% saturated ammonium sulfate was added. Then, impurities were removed by centrifugation. To this centrifuged supernatant, 60% saturated ammonium sulfate was added. Then, precipitates were collected by centrifugation. The precipitates were dissolved in the buffer solution of (2) containing 20% saturated ammonium sulfate, and subjected to Butyl-Toyopearl 650M column (TOSOH CORPORATION) that had been equilibrated by the buffer solution containing 20% saturated ammonium sulfate, and eluted at the concentration gradient of 20% to 0% of ammonium sulfate. The obtained pullulanase active fraction was dialyzed to buffer solution of (2), and subjected to HiLoad Q Sepharose Column (Amersham) that had been equilibrated by the same buffer solution, and eluted at the concentration gradient of 0 to 0.5 M of NaCl to obtain active fraction. This fraction was dialyzed to the buffer solution of (2), and subjected to Mono Q Column (Amersham) that had been equilibrated by the same buffer solution, and eluted at the concentration gradient of 0 to 0.5 M of NaCl to obtain purified *Bacillus subtilis* recombinant pullulanase. The analysis result of N-terminal amino acid sequence of this purified enzyme was MVSIRRSFEA and completely identity to gene sequence.

2. X-ray Analysis of *Bacillus subtilis* Pullulanase (1) Crystallization

Crystallization of *Bacillus subtilis* recombinant pullulanase was carried out by the following procedure. Firstly, screening was carried out by a sitting drop vapor diffusion method by using a 96-well plate (product by Emerald Biostructure and Hampton Research). After 24 hours at 20° C., small and thin crystal was observed in Wizard II No.8 well. Next, by changing the molecular weight and concentration of polyethylene glycol (PEG) or the concentration of buffer solution or salts, conditions were optimized. Finally, a crystal was obtained by a hanging drop vapor diffusion method by using a 24-well plate. The hanging drop (6 μl) consisting of 3 μl of enzyme solution (10 mg/ml) and 3 μl of reservoir solution (10% PEG4000, 0.1 M acetate buffer, pH 5.2, 0.2 M Mg $CH_3COO)_2$) was used and incubated for one to two days. Thus, diamond shaped crystal was obtained. Prior to the X-ray analysis, treatment with a reservoir solution containing 30% glycerol was carried out and then cooled instantly by using liquid nitrogen (−173° C.).

(2) X-ray Analysis

X-ray diffraction data were collected at a temperature of liquid nitrogen by using Synchrotron radiation BL-38B1 (SPring-8, Hyogo, Japan) and processed by using HKL2000 program. X-ray diffraction data of 2.1 Å resolution were collected so as to determine the crystallographic parameter. Space group was $P2_12_12_1$ and lattice constant was a=70.57 Å, b=127.68 Å, and c=189.25 Å.

(3) Determination of Three-dimensional Structure

A three-dimensional structure was determined at the resolution of 2.1 Å by a molecule substitution method using an atomic coordinate (PDB accession code 2FGZ) of pullulanase of *Klebsiella* pneumonia. The substitution of molecules and the refinement of structure were carried out by using program CNS_SOLVE ver. 11. Data related to statistics of data collection and refinement are shown in Table 1.

TABLE 1

| Crystal | *Bacillus subtilis* pullulanase |
|---|---|
| Data collection | Spring-8 BL38B1 |
| wavelength (Å) | 0.8 |
| detector | Jupiter 210 CCD |
| space group | $P2_12_12_1$ |
| lattice constant (Å) | A = 70.57, b = 127.68, c = 189.25 |
| resolution (Å) | 46.3-2.1 (2.18-2.10) |
| measured reflection | 590,744 (38,618) |
| unique reflection | 99,003 (9,775) |
| integrity (%) | 99.6 (99.6) |
| Rmerge (%) | 7.8 (31.4) |
| determination of structure | molecule substitution method |

TABLE 1-continued

Refinement

| | |
|---|---|
| Residues/Water/Ca2+/α-CD | 712 × 2, 673, 2, 0 |
| Resolution (Å) | 15.0-2.1 (2.17-2.1) |
| used reflection | 98,636 (8,725) |
| r.m.s. bond (Å), angle (°) | 0.005, 1.25 |
| R and Rfree | 0.201, 0.238 (0.224, 0.252) |

3. X-ray Analysis of *Bacillus subtilis* Pullulanase (in a State of Containing α-cyclodextrin (CD))

Sicne α-cyclodextrin (CD) is cyclic oligosaccharide and is an analog having a structure of amylose helix consisting of six glucose residues, it has often been used for studying as an inhibitor of an amylolytic enzyme such as amylase and pullulanase. In order to determine the substrate binding site of *Bacillus subtilis* pullulanase, an analysis of the three-dimensional structure of enzyme containing CD as a ligand (hereinafter, referred to as "CD-containing *Bacillus subtilis* pullulanase") was carried out. The analysis of the three-dimensional structure was carried out basically by the same method as 2. except that purified *Bacillus subtilis* recombinant pullulanase was prepared in 1. and 20 mM CD was added in the hanging drop at the time of crystallization. Data related to statistics about data collection and data are shown in Table 2.

TABLE 2

| | |
|---|---|
| Crystal | *Bacillus subtilis* pullulanase containing α-cyclodextrin |
| Data collection | Spring-8 BL38B1 |
| wavelength (Å) | 1.0 |
| detector | Jupiter 210 CCD |
| space group | $P2_12_12_1$ |
| lattice constant (Å) | A = 70.36, b = 127.86, c = 189.29 |
| resolution (Å) | 40.0-2.2 (2.28-2.20) |
| measured reflection | 4.08, 687 (35,910) |
| unique reflection | 87,392 (8,550) |
| integrity (%) | 99.8 (99.3) |
| Rmerge (%) | 9.2 (42.4) |
| determination of structure | molecule substitution method |
| Refinement | |
| Residues/Water/Ca2+/α-CD | 712 × 2, 673, 2, 2 |
| Resolution (Å) | 15.0-2.2 (2.28-2.2) |
| used reflection | 87,004 (8,495) |
| r.m.s. bond (Å), angle (°) | 0.005, 1.25 |
| R and Rfree | 0.197, 0.238 (0.249, 0.282) |

A model of the three-dimensional structure of the obtained CD-containing *Bacillus subtilis* pullulanase is shown in FIG. 1. Note here that data of atomic coordinate are shown in the last part of the specification.

4. Comparison Analysis Between Three-dimensional Structure of CD-containing *Bacillus subtilis* Pullulanase and Three-dimensional Structure of *Klebsiella pneumoniae* Pullulanase The three-dimensional structure of CD-containing *Bacillus subtilis* pullulanase obtained in 3. and the three-dimensional structure of *Klebsiella pneumoniae* pullulanase (J. Mol. Biol., 359 (3): 690-707 (2006), RCSB Protein Data Bank code 2FHF) were superimposed onto each other by Least Square method by using program TURBO-FRODO, α carbons of amino acids of 499 residues were common within 2 Å with the root means square deviation (r.m.s.d.) of 1.09 Å. FIG. 2 shows the superimposed results. FIG. 3 is an enlarged view showing a CD binding site. FIG. 3 shows a CD binding site with respect to *Bacillus subtilis* pullulanase and the binding site of maltotetraose with respect to *Klebsiella pneumoniae* pullulanase (G4) (see, non-patent document 1). An amino acid residue (upper stage) in a position capable of forming CD and hydrogen binding in *Bacillus subtilis* pullulanase is shown together with the corresponding amino acid residue (lower stage) in *Klebsiella pneumoniae* pullulanase. Furthermore, amino acid residue (lower stage) that has been deduced to be involved in binding to G4 in *Klebsiella pneumoniae* pullulanase and the corresponding amino acid residue (upper stage) in *Bacillus subtilis* pullulanase are also shown together.

Although a domain (N1 domain) in the N terminal region observed in *Klebsiella pneumoniae* pullulanase was not observed in *Bacillus subtilis* pullulanase, both enzymes were very similar to each other in a catalytic region and a domain (A domain) as a nucleus including a substrate binding region. Furthermore, a CD binding site of *Bacillus subtilis* pullulanase is in the vicinity of G4 binding site of *Klebsiella* pneumonia.

As shown in FIG. 3, in *Bacillus subtilis* pullulanase, twelve in total of amino acid residues that are thought to be involved in binding to the substrate were successfully identified as an amino acid position in the binding site of CD: Y292 (tyrosine the 292 position), G371 (glycine at the 371 position), D406 (aspartic acid at the 406 position), L407 (leucine at the 407 position), W437 (tryptophane at the 437 position), D465 (aspartic acid at the 465 position), T475 (threonine at the 475 position), F476 (phenyl alanine at the 476 position), D525 (aspartic acid at the 525 position), N526 (asparagine at the 526 position), N580 (asparagine at the 580 position), and Y582 (tyrosine at the 582 position). Furthermore, in *Klebsiella pneumoniae* pullulanase, amino acid corresponding to these amino acid residues, that is, Y559 (tyrosine at the 559 position), C643 (cysteine at the 643 position), D677 (aspartic acid at the 677 position), L678 (leucine at the 678 position), W708 (tryptophane at the 708 position), D734 (aspartic acid at the 734 position), P745 (proline at the 745 position), F746 (phenyl alanine at the 746 position), D834 (aspartic acid at the 834 position), N835 (asparagine at the 835 position), D890 (aspartic acid at the 890 position), and Y892 (tyrosine at the 892 position) were successfully determined. Among the thus determined amino acids, D677, W708, D734, D834, N835 and D890 were amino acids deduced to be involved in binding to G4 in the above-mentioned report.

Figure 4:
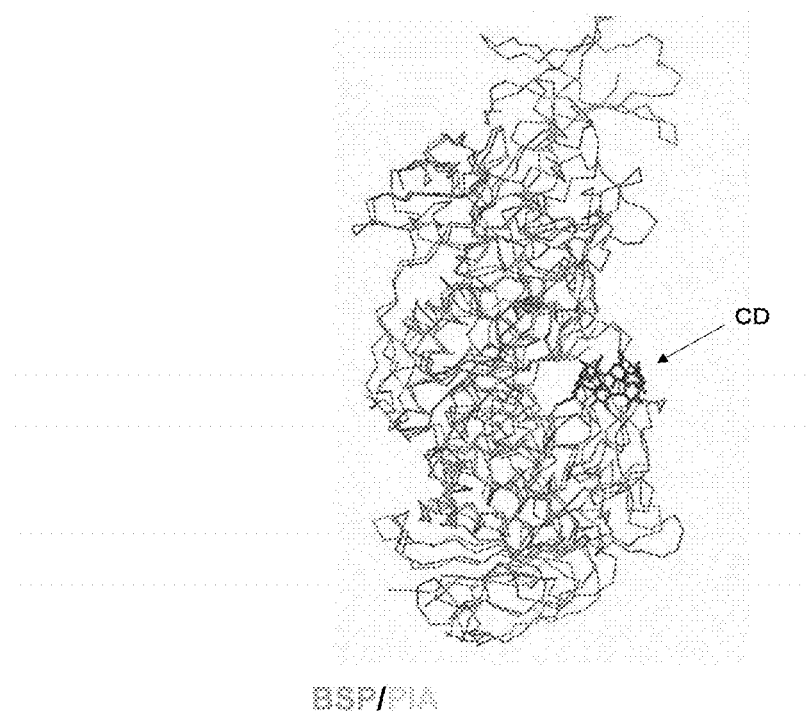
FIG. 4 is a view shown by superimposing *Bacillus subtilis* pullulanase (BSP) having α-cyclodextrin as a ligand and α carbon of isoamylase of *Pseudomonas amyloderamosa* (PIA) onto each other. CD: α-cyclodextrin.
Figure 5:
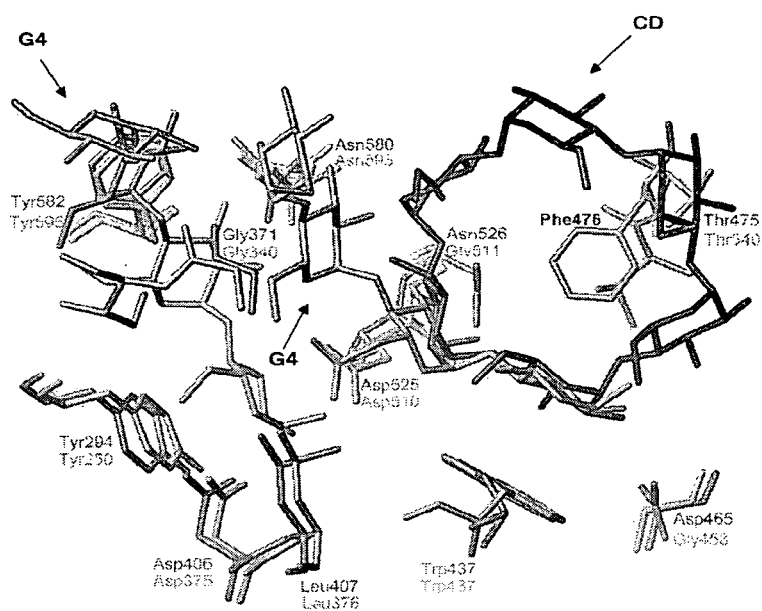
FIG. 5 is an enlarged view showing a substrate binding region of FIG. 4. CD: α-cyclodextrin, G4: maltotetraose. An amino acid of *Bacillus subtilis* pullulanase (upper stage) and an amino acid of isoamylase of *Pseudomonas amyloderamosa* (lower stage) corresponding to the amino acid of the upper stage are shown.

5. Comparison Analysis Between Three-dimensional Structure of CD-containing *Bacillus subtilis* Pullulanase and Three-dimensional Structure of *Pseudomonas amyloderamosa* Isoamylase The three-dimensional structure of CD-containing *Bacillus subtilis* pullulanase obtained in 3. and the three-dimensional structure of *Pseudomonas amyloderamosa* isoamylase (J. Mol Biol., 281 (5): 885-97 (1998), RCSB Protein Data Bank code 1BF2) were superimposed onto each other by Least Square method by using program TURBO-FRODO, α carbons of amino acids of 421 residues were common within 2 Å with the root means square deviation (r.m.s.d.) of 1.13 Å. FIG. 4 shows the superimposed results. FIG. 5 is an enlarged view showing a CD binding site.

The both enzymes do not have a domain (N1 domain) in the N terminal region observed in *Klebsiella pneumoniae* pullulanase and is very similar in domain (A domain) in terms of, for example, a nucleus including a catalytic region or a substrate binding region. The amino acid residue (upper stage) in the position capable of forming hydrogen binding to CD in *Bacillus subtilis* pullulanase is shown together with the corresponding amino acid residue (lower stage) in *Pseudomonas amyloderamosa* isoamylase. Furthermore, amino acid residues corresponding to the amino acids deduced to be involved in binding to G4 in *Klebsiella pneumoniae* pullulanase (upper stage: *Bacillus subtilis* pullulanase, and lower stage: *Pseudomonas amyloderamosa*).

Figure 6:
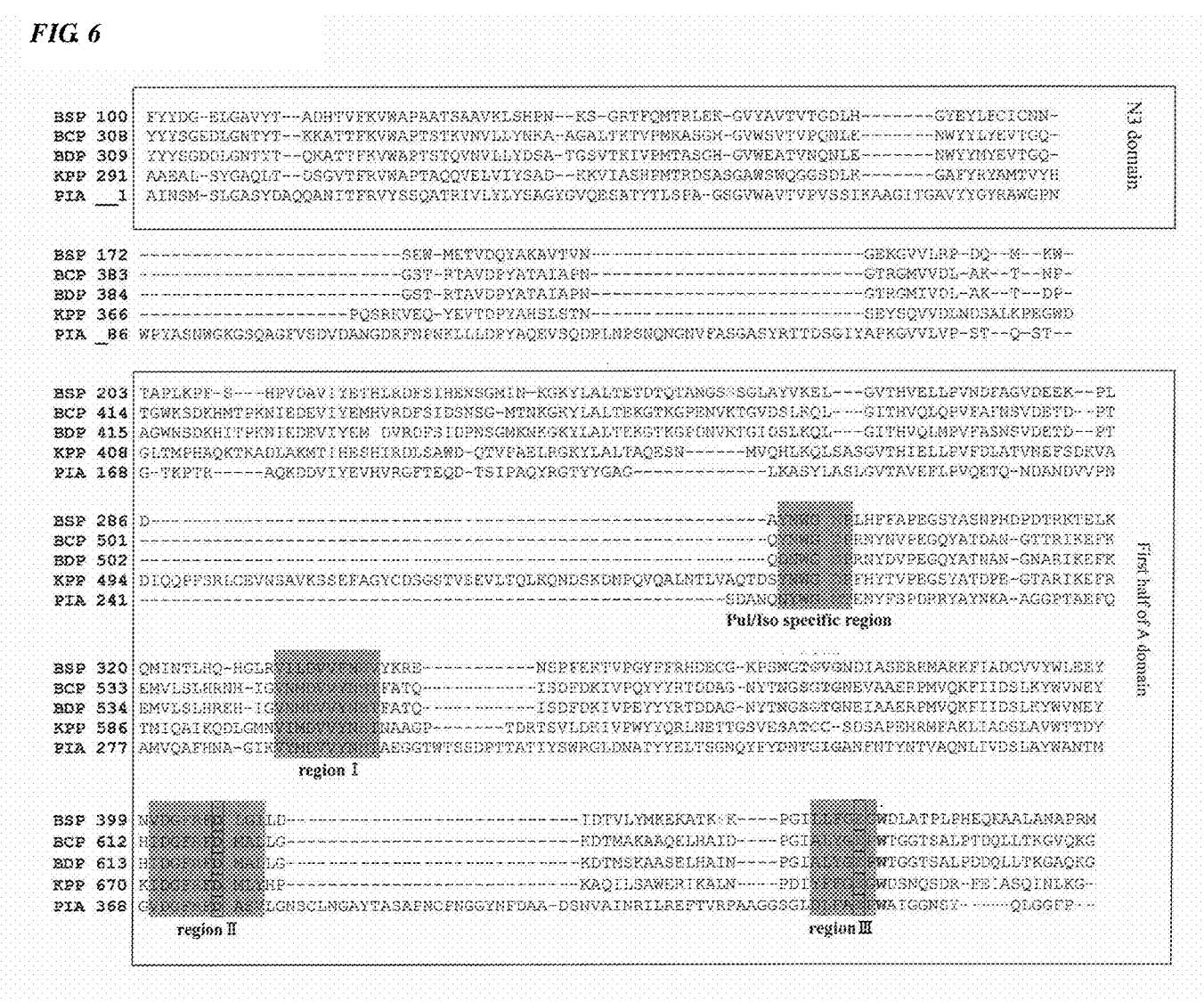
Figure 6:
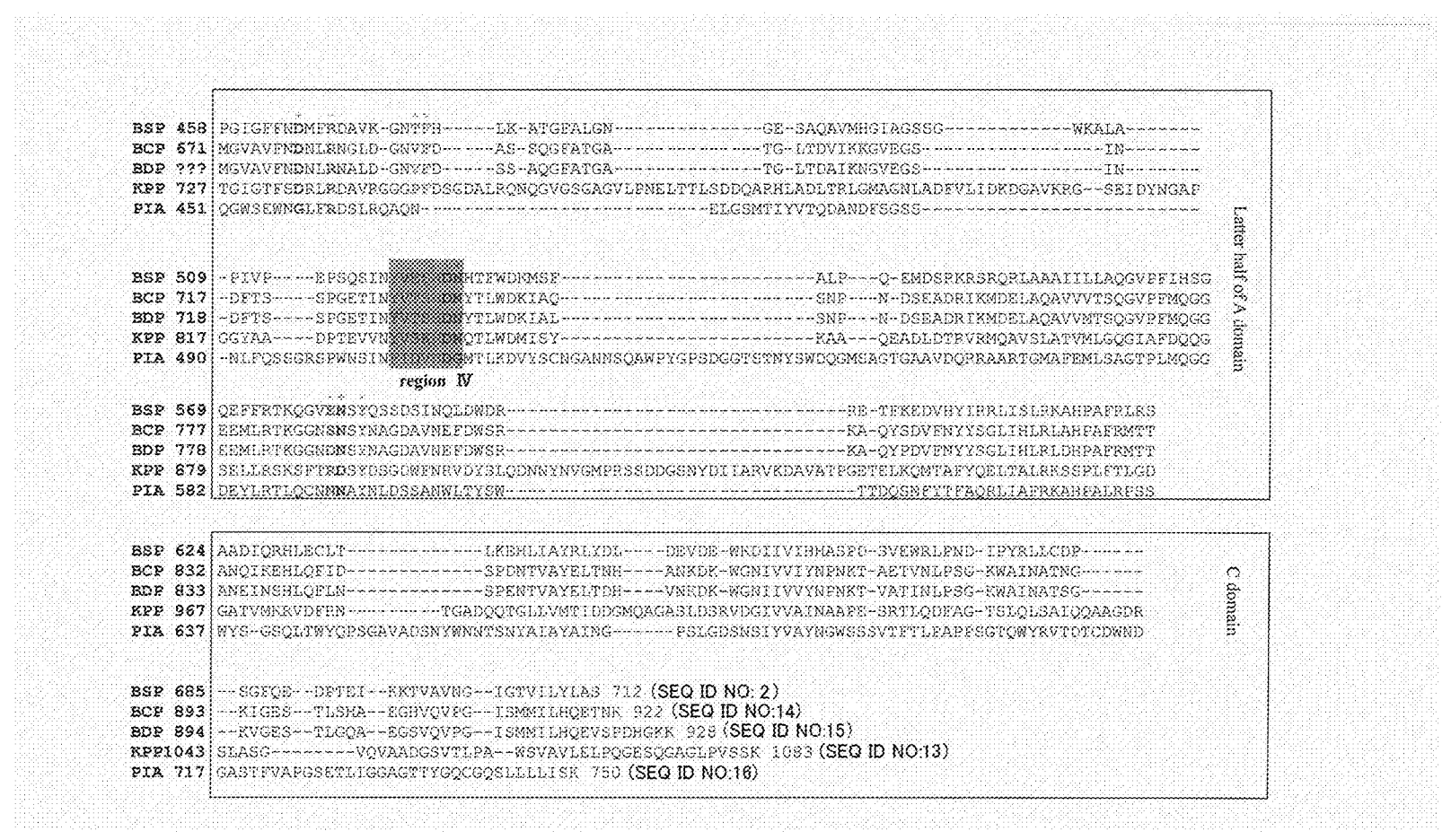

6. Formation of Alignment of Amino Acid Sequence Based on Three-dimensional Structure With the use of the result of comparison of the three-dimensional structures of CD-containing *Bacillus subtilis* pullulanase, *Klebsiella pneumoniae* pullulanase and *Pseudomonas amyloderamosa* isoamylase obtained in 4. and 5., alignments of amino acid sequences with respect to these three enzymes were formed based on the three-dimensional structures. Furthermore, alignments of amino acid sequences with respect to two kinds of pullulanases (pullulanase from *Bacillus* sp. APC-9603 and pullulanase from *Bacillus deramificans*) being derived from strains related to *Bacillus subtilis* and having a high homology in primary structure were formed by using ClustalW program. Alignments were formed with respect to five kinds of enzymes with these two alignments added (see FIG. 6). As shown in FIG. 6, these five kinds of enzymes have extremely high partial similarity. In addition, the result of alignment of the amino acid sequence of pullulanase of *Bacillus subtilis* (BSP) and the amino acid sequence of pullulanase of *Bacillus licheniformis* (BLP) is showed in FIG. 8. These two enzymes also have extremely high partial similarity.

7. Production of *Bacillus subtilis* Recombinant Pullulanase Mutant

Figure 7:
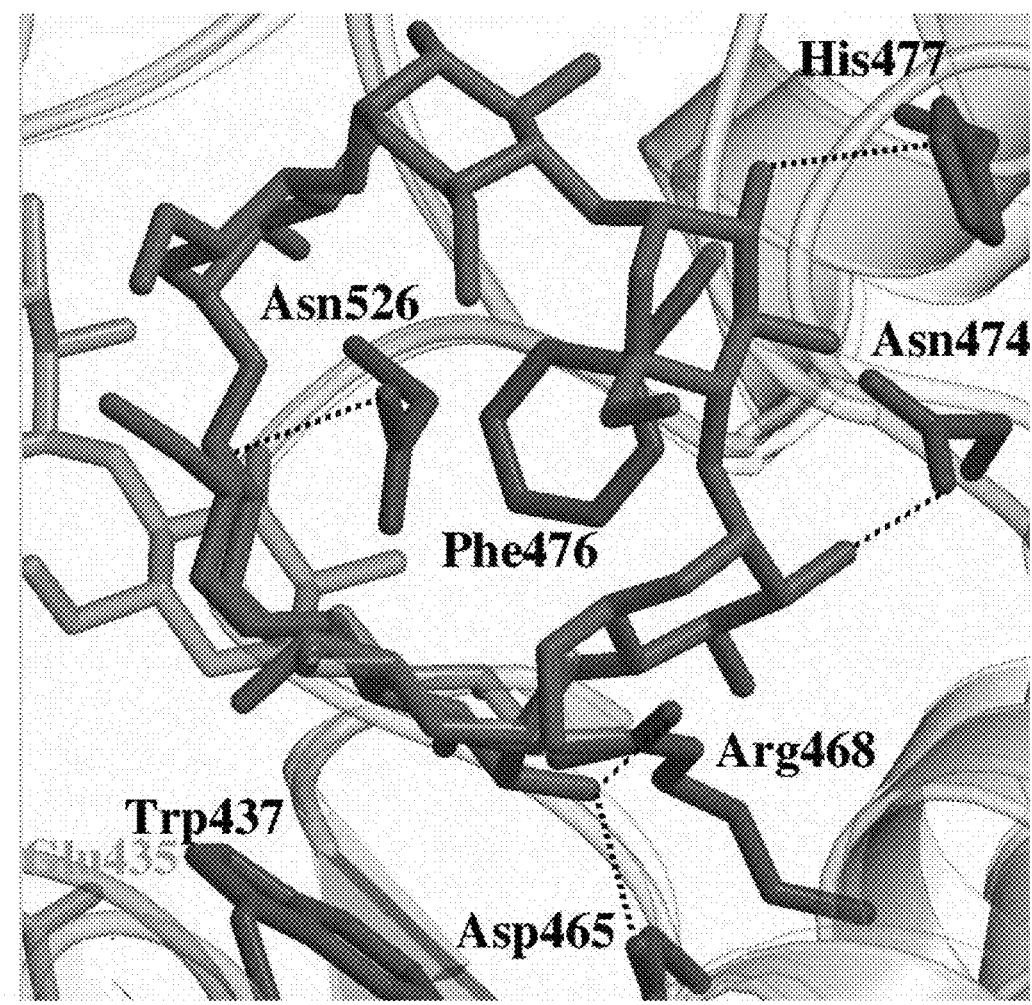
FIG. 7 is an enlarged view showing an α-cyclodextrin biding site of Ifg.

From the three-dimensional structure of *Bacillus subtilis* pullulanase to which CD obtained in 3. was bonded as a ligand, it is assumed that the side chain of Phe476 of *Bacillus subtilis* pullulanase is incorporated in the cyclic structure of the CD as a substrate analog (FIG. 7) and has something to do with the recognition of a substrate. Under this assumption, Phe476 was substituted with another amino acid by the following procedure and the effect thereof was verified.

Based on the sequence of gene AmyX encoding *Bacillus subtilis* pullulanase, a primer for substituting Phe476 with Gly or Ser was synthesized. In order to substitute Phe476 with Gly or Ser, forward primers and the corresponding reverse primers set forth in SEQ ID NOs: 5 and 6 were synthesized, respectively, and the concentration was adjusted to 100 ng/μl. By using an expression plasmid pEBSP of *Bacillus subtilis* recombinant pullulanase as a template, the following PCR reaction was carried out: 1.5 μl (30ng/μl) of pEBSP, 5 μl of 10×PCR buffer solution (one attached to the below-mentioned DNA polymerase), 1.0 μl (2.5 mM each) of dNTP, 1.25 μl each of mutated primer sets (forward and reverse primers), 39 μl of sterile water and 1 μl (2.5 U) of Pfu Turbo Hotstart DNA polymerase (Stratagene) were prepared; 30 cycles of reactions at 95° C. for 30 seconds (denaturation)—at 55° C. for 60 seconds (annealing)—at 68° C. for 12 minutes (elongation) were carried out; and finally amplification at 68° C. for 5 minutes was carried out. The obtained PCR product was confirmed by 1% agarose gel electrophoresis, and then the rest of the PCR product was treated with restriction enzyme Dpn I to degrade a methylated template plasmid and transformed to *Escherichia coli* competent cell DH5α strain. Plasmid DNA was isolated from the obtained ampicillin resistance transformant, the base sequence was confirmed and the intended mutated gene was obtained. A plasmid having the intended mutated gene was introduced into an expression host *Escherichia coli* HMS174 (DE3) strain to express and purify the mutated pullulanase of *Bacillus subtilis* similar to 1. (2) and (3).

```
                                              SEQ ID NO: 5
5'-GTAAAAGGGAACACCGGTCACCTTAAGGCAATA-3'

SEQ ID NO: 6
5'-GTAAAAGGGAACACCTCTCACCTTAAGGCAATA-3'
```

8. Substrate Specificity of *Bacillus subtilis* Recombinant Pullulanase Mutant

The kinetic parameters with respect to pullulan and amylopectin of *Bacillus subtilis* recombinant pullulanase mutant prepared in 4. were measure according to the method described in J Biochem (Tokyo), 116(6): 1264-8 (1994). Pullulan or amylopectin having various concentrations were dissolved in 50 mM acetate buffer (pH 5.6) and reacted at 25° C. The concentration of a reducing sugar contained in the regularly sampled reaction solution was determined by a Park-Johnson method (Park and Johnson, J. Biol. Chem. 1949 Nov; 181(1):149-51), and the reaction rate was measured from the increasing rate of the reducing sugar. Km value and Kcat value were obtained by curve fitting into Michaelis-Menten equation by the non-linear minimum square method. Results are shown in Table 3.

TABLE 3

| | pullulan | | amylopectin | |
|---|---|---|---|---|
| | Km (mg/ml) | k cat ($s^{-1}$) | Km (mg/ml) | k cat ($s^{-1}$) |
| wild type pullulanase | 14.93 | 4317 | 199.20 | 4121 |
| mutant type (F476G) | 20.45 | 5362 | 53.19 | 1198 |
| mutant type (F476S) | 645.16 | 10365 | 156.25 | 2146 |

When the wild type and the mutant types are compared with each other, they are shown to be different in the Km value and Kcat value. For example, in the mutant type (F476G: mutated enzyme in which an amino acid residue at the 476 position is changed from phenyl alanine to glycine), the Km value when amylopectin is used as a substrate is considerably lower than that of the wild type, which shows that the affinity to amylopectin is radically improved. Furthermore, in the mutant type (F476S: mutated enzyme in which an amino acid residue at the 476 position is changed from phenyl alanine to serine), the Km value when amylopectin is used as a substrate is lower than that of the wild type while the Km value when pullulan is used as a substrate is radically higher than that of the wild type, which shows that the substrate specificity has radically changed. Thus, introduction of mutation enabled the action property with respect to pullulan and amylopectin to be changed.

9. Cloning of *Klebsiella pneumoniae* Pullulanase Gene (1) Cloning of *Klebsiella pneumoniae* Pullulanase Gene Two primers (SEQ ID NOs: 7 and 8) were synthesized with reference to the base sequence of pullulanase of *Klebsiella aerogence* W70 strain (J. Bacteriol. 169 (5), 2301-2306 (1987) and J Bacteriol. 174(9): 3095.(1992), GenBank accession No. M16187). The PCR reaction was carried out under the following conditions by using chromosome DNA of *Klebsiella pneumoniae* ATCC9621 strain that had been isolated by the method by Sambrook et al. (Molecular Cloning: a laboratory manual, 2nd Edition, Cold Spring harbor Laboratory Press, 1989) as a template. The PCR reaction was carried out by using Accu TaqTM LA DNA polymerase system (Sigma), the reaction included one cycle of reaction at 98° C. for 30 seconds—at 59° C. for 20 seconds—at 68° C. for 3 minutes; 29 cycles of reaction at 98° C. for 15 seconds—at 59° C. for 20 seconds—at 68° C.

for 3 minutes; and reaction at 68° C. for 10 minutes of amplification was carried out. The obtained PCR fragment was subjected to TA cloning by using a pGEM-T vector (Promega). It was confirmed that the obtained PCR fragment encodes pullulanase correctly by determining the base sequence. The base sequence of the obtained PCR fragment and the amino acid sequence encoded thereby are shown in SEQ ID NO: 12 and SEQ ID NO: 13, respectively.

SEQ ID NO: 7
5'-TTATTGCCGGAGAGTGGCGA-3'

SEQ ID NO: 8
5'-CCAGACTGCTGACAAAGTGC-3'

(2) Expression of *Klebsiella pneumoniae* Pullulanase Gene

In order to construct an expression vector, primers shown in SEQ ID NOs: 9 and 10 were synthesized, and PCR reaction was carried out by using a pullulanase gene of *Klebsiella pneumoniae* as a template. The obtained PCR product was treated with restriction enzymes Nde I and Xba I, and linked to a plasmid pCold-I (TAKARA) to obtain an expression plasmid pCold-KPP of *Klebsiella pneumoniae* pullulanase. The plasmid was introduced into *Escherichia coli* JM109 (TAKARA) by transformation. Culture of the obtained transformant and purification of the expressed recombinant pullulanase were carried out according to the method described in 1.

SEQ ID NO: 9
5' - GGAATTCCATATGGATGTCGTCGTCCGCTTACCG -3'

(34 mer)

SEQ ID NO: 10
5' - GCTCTAGATTATTTACTGCTCACCGGCAG - 3' (29 mer)

10. Production of *Klebsiella pneumoniae* Pullulanase Mutant

The results obtained by analysis by superimposing the three-dimensional structure of CD-containing *Bacillus subtilis* pullulanase obtained in 3. and the three-dimensional structure of *Klebsiella pneumoniae* pullulanase (RCSB Protein Data Bank code 2FHF onto each other (FIGS. 2 and 3) and the results of amino acid sequence alignments (FIG. 6), an amino acid residue of pullulanase of *Klebsiella* pneumonia corresponding to Phe 476 residue that was thought to be involved in recognition of a substrate in *Bacillus subtilis* pullulanase was thought to be a Phe746 residue. Then, the Phe746 residue of pullulanase of *Klebsiella* pneumonia was substituted with Ala (or other amino acid).

Forward primers and the corresponding reverse primers set forth in SEQ ID NO: 11 were synthesized respectively in order to replace Phe746 with Ala in *Klebsiella pneumoniae*, and the concentration was adjusted to 100 ng/μl. By using an expression plasmid pCold-KPP of *Klebsiella pneumoniae* pullulanase as a template, the following PCR reaction was carried out: 1.5 μl (30 ng/μl) of pEBSP, 5 μl of 10×PCR buffer solution (one attached to the below-mentioned DNA polymerase), 1.0 μl (2.5 mM each) of dNTP, 1.25 μl each of mutated primer sets (forward and reverse primers), 39 μl of sterile water and 1 μl (2.5 U) of Pfu Turbo Hotstart DNA polymerase (Stratagene) were prepared; 30 cycles of reactions at 95° C. for 30 seconds (denaturation)—at 55° C. for 60 seconds (annealing)—at 68° C. for 12 minutes (elongation) were carried out; and finally amplification at 68° C. for 5 minutes was carried out. The obtained PCR product was confirmed by 1% agarose gel electrophoresis, and then the rest of the PCR product was treated with restriction enzyme Dpn I to degrade a methylated template plasmid and transformed to *Escherichia coli* competent cell DH5α strain. Plasmid DNA was isolated from the obtained ampicillin resistance transformant, the base sequence was confirmed and the intended mutated gene was obtained. A plasmid having the intended mutated gene was introduced into an expression host *Escherichia coli* HMS174 (DE3) strain to express and purify the mutated pullulanase of *Klebsiella pneumoniae* similar to 1. (2) and (3).

SEQ ID NO: 11
5'- GCCGGCCGACTCCGGTGAC-3'

11. Substrate Specificity of *Klebsiella pneumoniae* Pullulanase Mutant

The kinetic parameters with respect to pullulan and amylopectin of mutated pullulanase (F746A) and wild type pullulanase (WT) of *Klebsiella pneumoniae* prepared in 10. were measure according to the method described in J Biochem (Tokyo), 116(6): 1264-8 (1994). Pullulan or amylopectin having various concentrations were dissolved in 50 mM acetate buffer (pH 5.6) and reacted at 25° C. The concentration of a reducing sugar contained in the regularly sampled reaction solution was determined by a Park-Johnson method (Park and Johnson, J. Biol. Chem. 1949 November; 181(1):149-51), and the reaction rate was measured from the increasing rate of the reducing sugar. Km value and Kcat value were obtained by curve fitting into Michaelis-Menten equation by the non-linear minimum square method. Results are shown in Table 4.

TABLE 4

|  | pullulan | | amylopectin | |
| --- | --- | --- | --- | --- |
|  | Km (%) | Kcat ($s^{-1}$) | Km (%) | Kcat ($s^{-1}$) |
| wild type pullulanase | 0.00091 | 52.0 | 0.0063 | 7.0 |
| mutant type (F746A) | 0.00045 | 18.2 | 0.0083 | 5.2 |

Km value when pullulan was used for a substrate was lowered in the case of mutated enzyme as compared with the case of the wild type enzyme. On the other hand, Km value when amylopectin was used for a substrate was increased. From the results, it can be evaluated that in the mutated enzyme, the affinity to pullulan is improved (the affinity to amylopectin is lowered). Furthermore, Kcat value is different between the wild type and the mutant type. Thus, introduction of mutation enabled the action property with respect to pullulan and amylopectin to be changed.

Note here that the enzyme in which the affinity to a certain substrate is improved can act on a smaller amount of substrate. Such a property is advantageous in that the presence of the small amount of substrates is required to be measured.

INDUSTRIAL APPLICABILITY

A designing method and a preparation method of the present invention are used for improving an enzyme hydrolyzing an α-1,6-glycosidic linkage. With a mutated enzyme whose affinity and specificity to a substrate are improved, the increase in the yield of products and reduction of the amount of enzyme to be used (additive amount) can be achieved. On the other hand, it can be expected that the use of the designing method and the preparation method of the present invention provide a mutated enzyme usable to a novel application that has not been assumed with the use of wild type enzymes. That is to say, the present invention is capable of contributing to expansion of the applications of use of enzymes hydrolyzing an α-1,6-glycosidic linkage.

The present invention is not limited to the description of the above exemplary embodiments and Examples. A variety of modifications, which are within the scopes of the following claims and which are easily achieved by a person skilled in the art, are included in the present invention.

Contents of the theses, Publication of Patent Applications, Patent Publications, and other published documents referred to in this specification are herein incorporated by reference in its entity.

The atomic coordinates of three-dimensional structure of CD-containing *Bacillus subtilis* (*Bacillus subtilis* strain 168) are shown below.

Lengthy table referenced here

US09969996-20180515-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09969996B2). An electronic copy of the table will also be available from the USPTO upon request and payment of the fee set forth in 37 CFR 1.19(b)(3).

The invention claimed is:

1. A method for making a mutated pullulanase enzyme that has increased affinity for pullulan and hydrolyzes an α-1,6-glycosidic linkage, the method comprising following steps:
    (1) obtaining the amino acid sequence of a pullulanase enzyme having an amino acid sequence that is at least 95% identical to the amino acid sequence set forth in SEQ ID NO: 13;
    (2) identifying an amino acid to be mutated in the pullulanase enzyme of step (1), wherein said amino acid to be mutated corresponds to the amino acid at position $Phe^{746}$ of SEQ ID NO: 13;
    (3) constructing a mutated amino acid sequence by substituting the amino acid to be mutated with another amino acid or deleting the amino acid to be mutated, thereby making a mutated pullulanase enzyme having the mutated amino acid sequence that has increased affinity for pullulan and hydrolyzes an α-1,6-glycosidic linkage.

2. The method according to claim 1, wherein the identification of step (2) is achieved by a sequence alignment between SEQ ID NO: 13 and the amino acid sequence of the pullulanase enzyme of step (1).

3. A recombinant nucleic acid encoding the mutant pullulanase enzyme prepared by the method according to claim 1.

4. A transgenic microorganism comprising the recombinant nucleic acid of claim 3.

5. The method according to claim 1, wherein the identification of step (2) is achieved by a three-dimensional-structure comparison between SEQ ID NO: 13 and the amino acid sequence of the pullulananse enzyme of step (1).

* * * * *